United States Patent [19]

Abatjoglou et al.

[11] Patent Number: 5,113,022
[45] Date of Patent: May 12, 1992

[54] IONIC PHOSPHITES USED IN HOMOGENEOUS TRANSITION METAL CATALYZED PROCESSES

[75] Inventors: Anthony G. Abatjoglou, Charleston; David R. Bryant, South Charleston, both of W. Va.

[73] Assignee: Union Carbice Chemicals & Plastics Technology Corporation, Danbury, Conn.

[21] Appl. No.: 742,012

[22] Filed: Aug. 8, 1991

Related U.S. Application Data

[63] Continuation of Ser. No. 228,507, Aug. 5, 1988, Pat. No. 5,059,710.

[51] Int. Cl.⁵ .............................................. C07F 9/141
[52] U.S. Cl. .................................... 568/454; 502/162; 502/158; 502/167; 502/166; 568/909
[58] Field of Search ........................... 568/454, 909

[56] References Cited

U.S. PATENT DOCUMENTS

| | | | |
|---|---|---|---|
| 3,527,809 | 9/1970 | Pruett et al. | 568/454 |
| 4,148,830 | 4/1979 | Pruett et al. | 568/454 |
| 4,162,261 | 7/1979 | Kaplan | 260/449 L |
| 4,247,486 | 1/1981 | Brewester et al. | 568/454 |
| 4,248,802 | 2/1981 | Kuntz | 568/454 |
| 4,283,562 | 8/1981 | Billig et al. | 568/454 |
| 4,399,312 | 8/1983 | Russell et al. | 568/454 |
| 4,400,548 | 8/1983 | Abatjoglou et al. | 568/454 |
| 4,453,022 | 6/1984 | McCain et al. | 568/618 |
| 4,593,127 | 6/1986 | Bunning et al. | 568/454 |
| 4,599,206 | 7/1986 | Billig et al. | 568/454 |
| 4,633,021 | 12/1986 | Hanes | 568/454 |
| 4,673,701 | 6/1987 | Minagawa | 558/78 |
| 4,688,651 | 5/1987 | Billig et al. | 568/454 |
| 4,716,250 | 12/1987 | Abatjoglou et al. | 568/454 |
| 4,717,775 | 1/1988 | Billig et al. | 568/454 |
| 4,731,486 | 3/1988 | Abatjoglou et al. | 568/454 |
| 4,737,588 | 4/1988 | Billig et al. | 568/454 |
| 4,748,261 | 5/1988 | Billig et al. | 568/454 |
| 4,769,498 | 9/1988 | Billig et al. | 568/454 |
| 4,789,753 | 12/1988 | Billig et al. | 558/85 |
| 4,885,401 | 12/1989 | Billig et al. | 558/78 |
| 4,929,654 | 5/1990 | Wang et al. | 558/78 |

FOREIGN PATENT DOCUMENTS 0163234  4/1985  European Pat. Off.

OTHER PUBLICATIONS

92 Chemical Abstracts 774416 [J.P. 54/106561 (1979)].
Kirk-Othmer, "Encyclopedia of Chemical Technology," 3rd Ed., vol. 22, pp. 338-339 and 364-366 (1983).
"Introduction to modern liquid Chromatography" by L. R. Snyder et al, pp. 215-218 (1974).
"The Solubility of Non-Electrolytes" by J. H. Hildebrand et al. pp. 424-434 (1964).

Primary Examiner—Donald G. Daus
Attorney, Agent, or Firm—Reynold J. Finnegan

[57] ABSTRACT

This invention relates to novel ionic phosphites and the use thereof as ligands in homogenous transition metal catalyzed processes, especially hydroformylation.

14 Claims, No Drawings

IONIC PHOSPHITES USED IN HOMOGENEOUS TRANSITION METAL CATALYZED PROCESSES

This application is a continuation of prior U.S. application Ser. No. 228,507, filing date Aug. 5, 1988, now U.S. Pat. No. 5,059,710.

BACKGROUND OF THE INVENTION

1. Field of the Invention

This invention relates to novel ionic phosphites and the use thereof as ligands in homogenous transition metal catalyzed processes, especially hydroformylation.

2. Background of the Invention

Use of organic solubilized transition metal ligand complex catalysts is well known in the art of olefin hydroformylation, hydrosilation, hydrogenation, and oligomerization. In particular, olefinic compounds are hydroformylated with carbon monoxide and hydrogen to produce aldehydes in the presence of organic solubilized transition metal-phosphorus ligand complex catalysts.

It is known that the particular phosphorus ligand employed in such catalyzed hydroformylation processes may have a direct effect on the success of any given process. Moreover, selection of a particular phosphorus ligand to be used in any such transition metal catalyzed hydroformylation process depends upon the result desired, since the best overall processing efficiency may require a compromise between numerous factors. For example, in hydroformylation, such factors as aldehyde product selectivity (i.e., normal to branched chain aldehyde product ratio), catalyst reactivity and stability, and ligand stability often are of major concern in the selection of the desired phosphorus ligand to be employed.

For instance, U.S. Pat. No. 3,527,809 teaches how alpha-olefins can be selectively hydroformylated with rhodium-triorganophosphine or triorganophosphite ligand complexes to produce oxygenated products rich in normal aldehydes, while U.S. Pat. Nos. 4,148,830 and 4,247,486 disclose both liquid and gas recycle operations directed to the same result using a rhodium triarylphosphine ligand complex catalyst. U.S. Pat. No. 4,283,562 discloses that branched-alkylphenylphosphine or cycloalkylphenylphosphine ligands can be employed in a rhodium catalyzed hydroformylation process in order to provide a catalyst which is more stable against intrinsic deactivation. U.S. Pat. No. 4,400,548 discloses that bisphosphine monoxide ligands can be employed to provide rhodium complex catalysts of improved thermal stability useful for the hydroformylation production of aldehydes.

However, despite the obvious benefits attendant with the teachings of the patents mentioned above, the search continues for phosphorus ligands which provide improved characteristics, particularly with regard to ligand volatility.

For example, rhodium complex catalyzed hydroformylation processes preferably are carried out in a non-aqueous hydroformylation reaction medium containing both soluble catalyst complex and free phosphorus ligand, i.e., ligand not tied to or bound to the rhodium catalyst complex. In such processes, the desired aldehyde product is separated and recovered from the reaction product medium e.g. by distillation, and in continuous liquid catalyst recycle operations, the non-volatilized catalyst-ligand containing residue is recycled to the reactor. Accordingly, effective separation and recovery of the desired aldehyde product from its hydroformylation reaction product medium without excessive loss of phosphorus ligand and catalyst complex is important. Thus, in such non-aqueous hydroformylation processes, and in particular in liquid catalyst recycle processes, the volatility of the phosphorus ligand relative to the other components in the reaction medium also is of primary concern.

Removal (stripping) of phosphorus ligand with aldehyde product during distillation separation of product from reaction medium can result in not only high phosphorus ligand loss but also adverse changes in catalyst properties and catalyst deactivation. Indeed, if the rate of such simultaneous volatilization of the phosphorus ligand with aldehyde product is too high, an additional ligand recovery/recycle scheme may be required to make the process economical.

When low molecular weight olefins, such as propylene, are hydroformylated in non-aqueous systems using conventional tertiary phosphines such as triphenylphosphine, ligand relative volatility (re aldehyde product separation) is a concern, but is not an overwhelming problem. However, this problem is increased and magnified when the process is directed to the hydroformylation of longer chain olefinic compounds (e.g., $C_6$ to $C_{30}$ alpha-olefins) for producing the corresponding higher molecular weight aldehydes. Higher temperatures necessary to volatilize these higher molecular weight aldehyde products during separation from the hydroformylation reaction product medium also cause volatilization of such ligands.

A similar problem is presented when higher boiling aldehyde condensation by-products, such as trimers, are formed during hydroformylation and are desired to be separated, e.g., from catalyst-containing hydroformylation residues with further separate recovery of the hydroformylation catalyst and ligand. In this instance, the relative volatility of the ligand to the residue is important, without regard to whether such aldehyde condensation by-products are formed during the hydroformylation of low (e.g., $C_2-C_5$) molecular weight olefins or of high (e.g., $C_6-C_{30}$) molecular weight olefins.

Use of aqueous solutions of sulfonated arylphosphine compounds, such as the sulfonated triphenylphosphine salts disclosed in EPC 163234 and U.S. Pat. Nos. 4,248,802 and 4,399,312, as the phosphorus ligand in a hydroformylation process has been proposed to facilitate the separation and recovery of the rhodium complex catalyst and thus avoid the before-mentioned problems. Such prior art methods utilize a hydroformylation reaction medium comprised of both an organic phase containing the reaction starting materials and/or products and an aqueous or water phase containing the catalyst complex and free sulfonated phosphine ligands. A single phase non-aqueous hydroformylation reaction medium is not used in these methods. For efficient operation, such aqueous or water phase type hydroformylation reaction systems typically require high reactor pressures and/or high rhodium concentrations, and may also require buffers or phase transfer reagents and/or the use of larger and more costly processing equipment.

It has further been proposed to hydroformylate olefins in a non-aqueous reaction medium employing low volatile ionic phosphine ligands and a rhodium-phosphine ligand complex catalyst such as disclosed e.g., in U.S. Pat. Nos. 4,633,021 and 4,731,486 and such ligands can provide decided advantages in comparison to nonionic phosphine ligands. However, the search for other non-volatile phosphorus ligands which will provide at least similar, if not even better overall advantages, than such ionic phosphines remains a continuing one in the art of transition metal catalysis, and particularly in the olefin hydroformylation art.

DISCLOSURE OF THE INVENTION

It has now been discovered that certain ionic phosphite ligands may be employed as the phosphorus ligand in non-aqueous, homogeneous Group VIII transition metal-phosphorus complex catalyzed processes to provide numerous advantages. Although the following discussion emphasizes hydroformylation, it is to be understood that similar conditions may be encountered in the areas of hydrosilation, hydrogenation, and oligomerization, and this invention is considered applicable to these arts.

The ionic phosphite ligands described herein can be rendered soluble in organic media by using solubilizing agents, thus making them especially suitable for use as the phosphorus ligand in non-aqueous rhodium complex catalyzed hydroformylation processes designed to produce aldehyde products from both low and high molecular weight olefinic compounds. The low volatility and ability to solubilize these ionic phosphite ligands facilitates separation of the aldehyde product by vaporization (distillation) from the reaction product medium containing the rhodium complex catalyst and excess ligand. Even more conveniently, the ligands and complex catalyst may be separated or recovered by using processes, such as phase separation, which do not require selective vaporization. Thus, catalyst complex and ligand losses can be minimized, even when the non-aqueous hydroformylation process is directed to producing high molecular weight aldehyde products by hydroformylation of long chain olefins having 6 to 30 carbon atoms.

Other advantages of ionic phosphite ligands of this invention are the high catalyst activity and wide range of straight (normal) chain to branched (iso) chain aldehyde product ratios (product selectivity) of the hydroformylation process that can be obtained with such ligands. High catalyst activity and control over product selectivity are significant in hydroformylation processes since they allow one to maximize the yield of a desired aldehyde product.

The ionic phosphite ligands disclosed herein contain at least one ionic moiety selected from the group consisting of salts of carboxylic acid and of sulfonic acid, substituted on an aryl moiety of the ligand. Such salts contain that number of organic or inorganic cations needed to balance the charge of the acid anion of said ionic moiety.

It is an object of this invention to provide such ionic phosphite ligands.

It is another object of this invention to provide an improved homogeneous catalyzed process wherein said process is carried out in an organic, non-aqueous reaction medium containing an organic solubilized Group VIII transition metal-ionic phosphite ligand complex catalyst.

Other objects and advantages of this invention will become readily apparent from the following written description and appended claims.

Accordingly, this invention provides ionic phosphites selected from the group consisting of (i) poly-phosphites having the formula

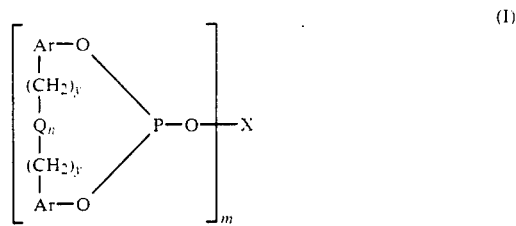

wherein each Ar group represents an identical or different aryl radical; wherein X represents an m-valent hydrocarbon radical selected from the group consisting of alkylene, alkylene-oxy-alkylene, aryl, and aryl—$(CH_2)_y$—$(Q)_n$—$(CH_2)_y$—aryl; wherein each y individually has a value of 0 or 1; wherein each Q individually represents a divalent bridging group selected from the class consisting of —$CR^1R^2$—, —O—, —S—, —$NR^3$—, —$SiR^4R^5$—, and —CO—, wherein $R^1$ and $R^2$ each individually represents a radical selected from the group consisting of hydrogen, alkyl of 1 to 12 carbon atoms, phenyl, tolyl and anisyl, wherein $R^3$, $R^4$, and $R^5$ each individually represents —H or —$CH_3$; wherein each n individually has a value of 0 to 1; wherein m has a value of 2 to 6; and wherein the poly-phosphites of formula (I) contain at least one ionic moiety selected from the group consisting of salts of carboxylic acid and of sulfonic acid, substituted on an aryl moiety of Ar or X;

(ii) diorganophosphites having the formula

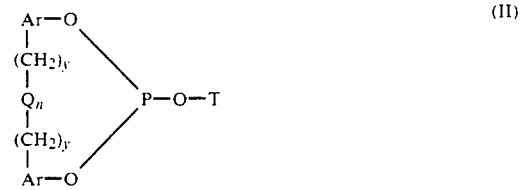

wherein T represents a monovalent hydrocarbon radical; wherein Ar, Q, n, and y are as defined above; and wherein the diorganophosphites of formula (II) contain at least one moiety selected from the group consisting of salts of carboxylic acid and of sulfonic acid, substituted on an aryl moiety of Ar or T; and (iii) open-ended bis-phosphites having the formula

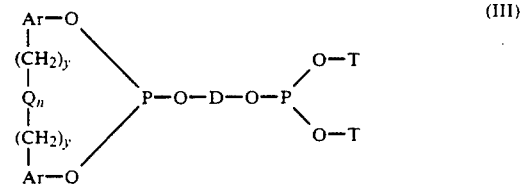

wherein D represents a divalent bridging group selected from the group consisting of alkylene, alkylene-oxy-alkylene, aryl, and aryl—$(CH_2)_y$—$Q_n$—$(CH_2)_y$—aryl; wherein Ar, Q, n, y, and T are as defined above and each T may be identical or different; and wherein the bis-phosphites of formula (III) contain at least one ionic moiety selected from the group consisting of salts of carboxylic acid and of sulfonic acid, substituted on an aryl moiety of Ar, D or T.

This invention also relates to employing said ionic phosphite ligands in a homogeneously catalyzed process utilizing an organic solubilized Group VIII transition metal-ionic phosphite ligand complex catalyst. Further, a generic aspect of this invention related to hydroformylation can be described as an improved non-aqueous hydroformylation process for producing aldehydes which comprises reacting an olefinically unsaturated organic compound with carbon monoxide and hydrogen in a non-aqueous hydroformylation reaction medium, said reaction medium containing an organic-solubilized Group VIII transition metal-phosphorus ligand complex catalyst and free phosphorus ligand, the improvement comprising employing the above-described ionic phosphites as both the phosphorus ligand of said complex catalyst and the free phosphorus ligand.

DETAILED DESCRIPTION

Accordingly, the subject invention encompasses use of novel ionic phosphite ligands in known homogeneous transition metal catalyzed processes conducted in a non-aqueous reaction medium containing an organic solubilized Group VIII transition metal-phosphorus ligand complex catalyst and free phosphorus ligand, especially non-aqueous hydroformylation processes for producing aldehydes by reacting an olefinically unsaturated compound with carbon monoxide and hydrogen. In the present invention, both the phosphorus ligand of said catalyst and the free phosphorus ligand are solubilized ionic phosphites, disclosed herein. Such hydroformylation (oxo synthesis) processes are well-known in the art; see, for example, U.S. Pat. Nos. 3,527,809, 4,148,830, 4,247,486, 4,633,021, and 4,731,486, the disclosures of which are hereby incorporated by reference. In accordance with this invention, any of the known reaction conditions and processing techniques heretofore employed in such conventional hydroformylation reactions may be utilized.

For instance, the hydroformylation process can be conducted in continuous, semi-continuous, or batch fashion and may involve any liquid and/or gas recycle operation, as desired. Likewise, the manner or order of addition of the reaction ingredients, catalysts, ligand, and/or solvent may be accomplished in any conventional fashion.

As noted, the hydroformylation reaction is carried out in a non-aqueous, organic hydroformylation reaction medium that contains both the organic solubilized Group VIII transition metal-ionic phosphite ligand complex catalyst and free ionic phosphite ligand. By "free ligand" is meant phosphorus ligand that has not formed a complex with a Group VIII transition metal atom. Moreover, as used herein, the term "non-aqueous" means that the hydroformylation process of this invention is conducted in the absence or essential absence of water, which is to say that any water, if present at all, in the hydroformylation reaction medium, is not present in an amount sufficient to unduly adversely affect the performance of the catalyst or cause undue degradation of the ionic phosphite ligand.

As noted above, ionic phosphite ligands used in this invention are selected from the group consisting of (i) poly-phosphites having the formula

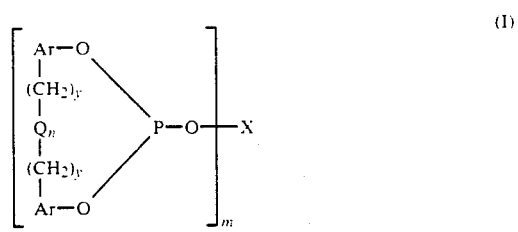

(ii) diorganophosphites having the formula

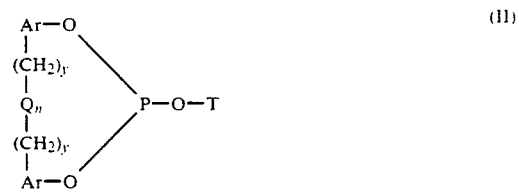

and (iii) open-ended bis-phosphites having the formula

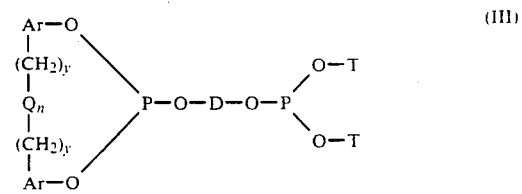

wherein each formula is as defined above.

Illustrative aryl radicals of the above-defined Ar, X, D and T groups of the above formulae include aryl moieties which may contain from 6 to 18 carbon atoms such as phenylene, naphthylene, anthracylene, and the like.

Moreover, as noted above, while any given ionic phosphite in the above formulae must contain at least one ionic moiety selected from the group consisting of salts of sulfonic acid and of carboxylic acid substituted on an aryl moiety of the above defined Ar, X, D and T groups, it is to be understood that any given phosphite may contain more than one such ionic moiety and such may also be the case with regard to any given aryl moiety in each ionic phosphite, provided that the total number of such ionic moieties in the given phosphite is not so high as to unduly adversely affect the organic solubility of the ionic phosphite ligand. Thus each ionic phosphite ligand preferably contains from 1 to 3 such ionic moieties, more preferably from 1 to 2 such ionic moieties, and more preferably 1 such ionic moiety. Moreover, it is preferred that only one such ionic moiety be substituted on any given aryl moiety in the ionic phosphite ligand when the ligand contains more than one such ionic moiety.

In the above formulae, preferably, m is from 2 to 4, and each y and each n has a value of 0. However, when n is 1, Q preferably is a $-CR^1R^2-$ bridging group as defined above and more preferably methylene $(-CH_2-)$ or alkylidene $(-CHR^2-)$, wherein $R^2$ is an alkyl radical of 1 to 12 carbon atoms (e.g. methyl, ethyl, propyl, isopropyl, butyl, dodecyl, etc.), especially methyl.

The m-valent hydrocarbon radicals represented by X in the ionic poly-phosphite ligands of formula I above are hydrocarbons containing from 2 to 30 carbon atoms selected from the group consisting of alkylene, alkylene-oxy-alkylene, aryl, and aryl-$(CH_2)_y$—$(Q)_n$—$(CH_2)_y$—aryl radicals, wherein Q, n and y are the same as defined above. Preferably the alkylene moieties of said radicals contain from 2 to 18 carbon atoms and more preferably from 2 to 12 carbon atoms, while the aryl moieties of said radicals preferably contain from 6 to 18 carbon atoms.

The divalent bridging group represented by D in the open-ended bis-phosphite ligands of formula III above are divalent hydrocarbons containing from 2 to 30 carbon atoms selected from the group consisting of alkylene, alkylene-oxy-alkylene, aryl and aryl-$(CH_2)_y$—$(Q)_n$—$(CH_2)_y$-aryl radicals, wherein Q, n and y are the same as defined above. Preferably the alkylene moieties of said radicals contain from 2 to 18 carbon atoms and more preferably from 2 to 12 carbon atoms, while the aryl moieties of said radicals preferably contain from 6 to 18 carbon atoms.

Hydrocarbon radicals represented by T in the above ionic phosphite ligand formulae include monovalent hydrocarbon radicals containing from 1 to 30 carbon atoms selected from the group consisting of alkyl radicals including linear or branched primary, secondary, or tertiary alkyl radicals, such as methyl, ethyl, n-propyl, isopropyl, amyl, sec-amyl, t-amyl, 2-ethylhexyl, and the like; aryl radicals such as phenyl, naphthyl, and the like; aralkyl radicals such as benzyl, phenylethyl, tri-phenylmethylethane, and the like; alkaryl radicals such as tolyl, xylyl, and the like; and cycloalkyl radicals such as cyclopentyl, cyclohexyl, cyclohexylethyl, and the like.

Preferably, T is selected from the group consisting of alkyl and aryl radicals which contain from about 1 and 30 carbon atoms. Preferably, the alkyl radicals contain from 1 to 18 carbon atoms, most preferably from 1 to 10 carbon atoms, while the aryl, aralkyl, alkaryl, and cycloalkyl radicals preferably contain from 6 to 18 carbon atoms. Further, although each T group in an ionic phosphite molecule of formula (III) may differ from the other, preferably they are identical.

Of course it is to be further understood that in addition to being substituted with an ionic moiety as described above, the aryl moieties of the defined Ar, X, D and T groups in the above formulae may also be substituted with any other substituent radical that does not unduly adversely affect the process of this invention. Illustrative substituents include radicals containing from 1 to 18 carbon atoms such as alkyl, aryl, aralkyl, alkaryl and cycloalkyl radicals; alkoxy radicals; silyl radicals such as —$Si(R^9)_3$ and —$Si(OR^9)_3$; amino radicals such as —$N(R^9)_2$; acyl radicals such as —$C(O)R^9$; acyloxy radicals such as —$OC(O)R^9$; carbonyloxy radicals such as —$COOR^9$; amido radicals such as —$C(O)N(R^9)_2$ and —$N(R^9)COR^9$; sulfonyl radicals such as —$SO_2R^9$; sulfinyl radicals such as —$SO(R^9)_2$; thionyl radicals such as —$SR^9$; phosphonyl radicals such as —$P(O)(R^9)_2$; as well as halogen, nitro, cyano, trifluoromethyl, and hydroxy radicals, and the like, wherein each $R^9$ can be a monovalent hydrocarbon radical such as alkyl, aryl, alkaryl, aralkyl, and cycloalkyl radicals, with the provisos that in amino substitutents such as —$N(R^9)_2$, each $R^9$ taken together can also comprise a divalent bridging group that forms a heterocyclic radical with the nitrogen atom, in amido substituents such as —$C(O)N(R^9)_2$ and —$N(R^9)COR^9$, each bonded to N can also be hydrogen, and in phosphonyl substituents such as —$P(O)(R^9)_2$, one $R^9$ can be hydrogen. Of course, it is to be understood that each $R^9$ group in a particular substituent may be the same or different. Of course, such hydrocarbon substituent radicals could possibly in turn be substituted with a substituent such as already herein outlined above provided that any such occurrence would not unduly adversely effect the process of this invention.

Among the more preferred ionic phosphite ligands are those wherein the two Ar groups linked by the bridging group represented by —$(CH_2)_y$—$(Q)_n$—$(CH_2)_y$— in the above formulae are bonded through their ortho positions in relation to the oxygen atoms that connect the Ar groups to the phosphorus atom. It is also preferred that any substituent radial, when present on such Ar groups, be bonded in the para and/or ortho position on the aryl in relation to the oxygen atom that bonds the substituted Ar group to its phosphorus atom.

Accordingly, a preferred class of ionic phosphite ligands employable in this invention are those of the formulae:

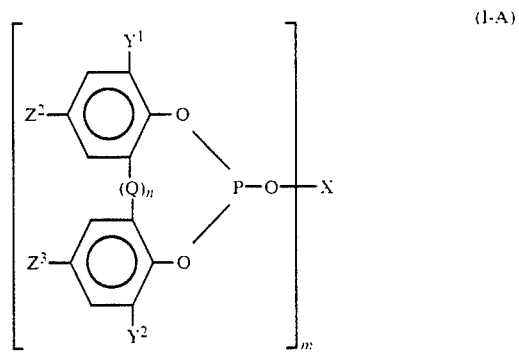

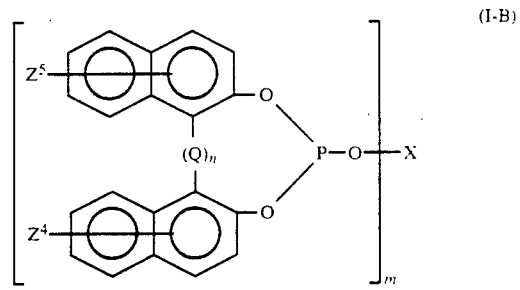

wherein each $Y^1$, $Y^2$, $Z^2$, $Z^3$, $Z^4$ and $Z^5$ group individually represents a radical selected from the group consisting of hydrogen, monovalent hydrocarbon radicals containing from 1 to 18 carbon atoms (e.g. alkyl, aryl, alkaryl, aralkyl, and cycloalkyl radicals), hydroxy, alkoxy radicals containing from 1 to 10 carbon atoms, and salts of sulfonic acid and of carboxylic acid; wherein X represents an m-valent bridging group containing from 6 to 30 carbon atoms selected from the group consisting of aryl and aryl-$Q_n$-aryl radicals; wherein m has a value of 2 to 4; wherein each Q radical individually represents —$CR^1R^2$— wherein $R^1$ and $R^2$ each individually represent a radical selected from the group consisting of hydrogen and alkyl of 1 to 12 carbon atoms; and wherein n has a value of 0 or 1; with the proviso that in each phosphite ligand of formulae I-A and I-B above, either at least one $Y^1$, $Y^2$, $Z^2$, $Z^3$, $Z^4$ and $Z^5$ group is an ionic moiety selected from the group consisting of salts of sulfonic acid and of carboxylic acid, or each said ligand contains at least one such ionic moiety substituted on an aryl moiety of X.

Another preferred class of ionic phosphite ligands employable in this invention are those of the formulae

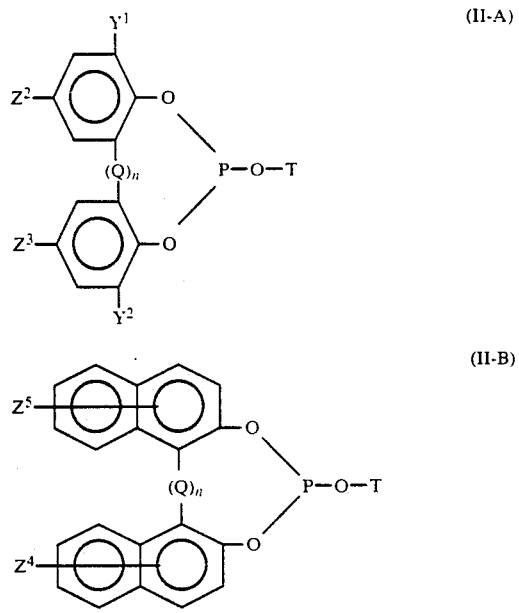

(II-A)

(II-B)

wherein $Y^1$, $Y^2$, $Z^2$, $Z^3$, $Z^4$, $Z^5$, Q and n are the same as defined above in formulae I-A and I-B; wherein T represents a monovalent hydrocarbon radical containing from 1 to 30 carbon atoms selected from the group consisting of alkyl, aryl, aralkyl, alkaryl or cycloalkyl radicals; with the proviso that in each phosphite ligand of formulae II-A and II-B above, either at least one $Y^1$, $Y^2$, $Z^2$, $Z^3$, $Z^4$ and $Z^5$ group is an ionic moiety selected from the group consisting of salts of sulfonic acid and of carboxylic acid, or each said ligand contains at least one such ionic moiety substituted on an aryl moiety of T.

Yet another preferred class of ionic phosphite ligands employable in this invention are those of the formulae

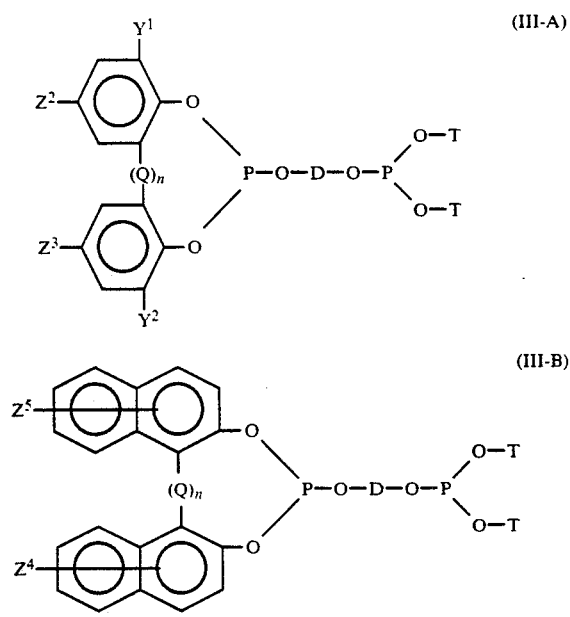

(III-A)

(III-B)

wherein D represents a divalent bridging group containing from 6 to 30 carbon atoms selected from the group consisting of aryl and aryl-$Q_n$-aryl radicals; and wherein $Y^1$, $Y^2$, $Z^2$, $Z^3$, $Z^4$, $Z^5$, Q, n and each T are the same as defined above in formulas I-A, I-B, II-A and II-B; and wherein each T can be the same or different; with the proviso that in each phosphite ligand of formulas III-A and III-B above, either at least one $Y^1$, $Y^2$, $Z^2$, $Z^3$, $Z^4$, and $Z^5$ group is an ionic moiety selected from the group consisting of salts of sulfonic acid and of carboxylic acid, or each said ligand contains at least one such ionic moiety substituted on an aryl moiety of D or T.

A number of preferred embodiments of the above ionic phosphite ligand formulae may be found already herein discussed above, e.g. most preferably m has value of 2 and each y and n has a value of 0, while Q is preferably —$CH_2$— or —$CHCH_3$—. Further each ionic phosphite preferably contains from 1 to 3 such ionic moieties as defined herein, more preferably from 1 to 2 such ionic moieties and most preferably only one such ionic moiety.

The ionic moieties of the ionic phosphite ligand formulae above are salts of sulfonic acid and of carboxylic acid. Such salts contain that number of organic or inorganic cations needed to balance the charge of the acid anions substituted onto the phosphite ligand. Suitable inorganic cations are selected from the group consisting of alkali metals and alkaline earth metals. Illustrative alkali metal cations include lithium ($Li+$), sodium ($Na+$), potassium ($K+$), cesium ($Cs+$), and rubidium ($Rb+$), while illustrative alkaline earth metal cations include calcium ($Ca++$), barium ($Ba++$), magnesium ($Mg++$), and strontium ($Sr++$). Suitable organic cations are selected from the group consisting of quaternary ammonium cations having the formula $[N(R^{21})(R^{22})(R^{23})(R^{24})]+$, wherein $R^{21}$, $R^{22}$, $R^{23}$, and $R^{24}$ each represents hydrogen or a radical containing from 1 to 30 carbon atoms selected from the group consisting of alkyl, aryl, alkaryl, aralkyl, and cycloalkyl radicals, and wherein any two or three of said $R^{21}$, $R^{22}$, $R^{23}$, and $R^{24}$ groups can be bonded together to form a mono-, bi-, or poly-cyclic ring along with the nitrogen atom of said cation. The preferred cation is an alkali metal or alkaline earth metal cation.

Illustrative m-valent hydrocarbon radicals represented by X in the above formulae include substituted and unsubstituted hydrocarbon radicals containing from 2 to about 30 carbon atoms selected from the group consisting of alkylene, alkylene-oxy-alkylene, phenylene, naphthylene, phenylene-$(CH_2)_y$—(Q-$)_n$—$(CH_2)_y$-phenylene and naphthylene-$(CH_2)_y$—(Q-$)_n$—$(CH_2)_y$-naphthylene radicals, and where Q, n, and y are the same as defined above. More specific illustrative m-valent hydrocarbon radicals represented by X include e.g. straight or branched chain alkylene radicals such as —$(CH_2)_x$ wherein x has a value of 2 to 18 (preferably 2 to 12), pentaerythritol, which yields an m-valent hydrocarbon radical of formula $C(CH_2OH)_{4-m}(CH_2)_m$, 1,2,6-hexylene, and the like; —$CH_2CH_2OCH_2CH_2$—; 1,4-phenylene, 2,3-phenylene, 1,3,5-phenylene, 1,3-phenylene, 1,4-naphthylene, 1,5-naphthylene, 1,8-naphthylene, 2,3-naphthylene, 1,1'-biphenyl-2,2'-diyl, 2,2'-biphenyl-1,1'-diyl, 1,1'-biphenyl-4,4'-diyl, 1,1'-binaphthyl-2,2'-diyl, 2,2-binaphthtyl-1,1'-diyl, phenylene-$CH_2$-phenylene, phenylene-S-phenylene, $CH_2$-phenylene-$CH_2$, phenylene-$CH(CH_3)$-phenylene radicals and the like.

Preferred ionic poly-phosphite ligands of formula (I) include close-ended bis-phosphites wherein X in the above ionic phosphite formulae is a divalent radical selected from the group consisting of phenylene, naphthylene, naphthylene-(Q)$_n$-naphthylene, and phenylene-(Q)$_n$-phenylene radicals, wherein Q and n are the same as both generically and preferably defined above. Of course the aryl moieties of such X radicals can contain substituent radicals such as disclosed and discussed herein.

Divalent radical D in ionic phosphite formula (III) above can be the same as any m-valent radical, as described for X herein, wherein m=2. Further preferred open-ended bis-phosphite ligands include those wherein D is a divalent radical selected from the group consisting of phenylene, naphthylene, naphthylene-(Q)$_n$-naphthylene, and phenylene-(Q)$_n$-phenylene radicals wherein Q and n are the same as both generically and preferably defined above. Of course the aryl moieties of such D radicals can contain substituent radicals such as disclosed and discussed herein.

Among the more preferred bis-phosphite ligands of formula (I) and open-ended bis-phosphite ligands of formula (III) are those wherein the naphthylene radical represented by X or D is selected from the group consisting of 1,2-naphthylene, 2,3-naphthylene, and especially 1,8-naphthylene, and those wherein the two phenylene radicals or two naphthylene radicals of X or D linked by the bridging group represented by —(Q)$_n$— are bonded through their ortho positions in relation to the oxygen atoms that connect the two phenylene or two naphthylene radicals to their phosphorus atom. It is also preferred than any substituent radical when present on such phenylene or naphthylene radicals be bonded in the para and/or ortho position of the phenylene or naphthylene radical in relation to the oxygen atom that bonds the given substituted phenylene or naphthylene radical to its phosphorus atom.

Hydrocarbon radicals represented by T in the above ionic phosphite ligand formulae include monovalent hydrocarbon radicals containing from 1 to 30 carbon atoms selected from the group consisting of alkyl radicals including linear or branched primary, secondary, or tertiary alkyl radicals, such as methyl, ethyl, n-propyl, isopropyl, amyl, sec-amyl, t-amyl, 2-ethylhexyl, 1-decyl, and the like; aryl radicals such as phenyl, naphthyl, and the like; aralkyl radicals such as benzyl, phenylethyl, tri-phenylmethylethane, and the like; alkaryl radicals such as tolyl, xylyl, and the like; and alicyclic radicals such as cyclopentyl, cyclohexylethyl, and the like.

Preferably, T is selected from the group consisting of alkyl and aryl radicals which contain between about 1 to 30 carbon atoms. Preferably, the alkyl radicals contain from 1 to 18 carbon atoms, most preferably from 1 to 10 carbon atoms, while the aryl, aralkyl, alkaryl, and alicyclic radicals preferably contain from 6 to 18 carbon atoms. Further, although each T group in an ionic phosphite molecule of formula (III) may differ from the other, preferably they are identical.

Further preferred aryl radicals represented by T include those having the formula

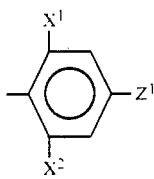

wherein $X^1$, $X^2$, and $Z^1$ each individually represents a radical as defined for $Y^1$, $Y^2$, $Z^2$ and $Z^3$ hereinbefore. More preferably $X^1$ and $X^2$ are the same or different and represent hydrogen or a radical having a steric hindrance of isopropyl or greater and $Z^1$ represents an ionic moiety as defined herein.

Moreover, as noted, the above-described radicals represented by Ar, X, D and T of the above formulae, may be further substituted with any substituent that does not unduly adversely effect the desired results of this invention. Illustrative substituents are, for example, monovalent hydrocarbon radicals having between one and about 18 carbon atoms, such as alkyl, aryl, alkaryl, aralkyl, cycloalkyl and other radials, as defined above. In addition various nonhydrocarbon substituents that may be present include e.g. halogen, preferably chlorine or fluorine, —NO$_2$, —CN, —CF$_3$, —OH, —Si(CH$_3$)$_3$, —Si(OCH$_3$)$_3$, —Si(C$_3$H$_7$)$_3$, —C(O)CH$_3$, —C(O)C$_2$H$_5$, —OC(O)C$_6$H$_5$, —C(O)OCH$_3$, —N(CH$_3$)$_2$, —NH$_2$, —NHCH$_3$, —NH(C$_2$H$_5$), —CONH$_2$, —CON(CH$_3$)$_2$, —S(O)$_2$C$_2$H$_5$, —OCH$_3$, —OC$_2$H$_5$, —OC$_6$H$_5$, —C(O)C$_6$H$_5$, —O(t—C$_4$H$_9$), —SC$_2$H$_5$, —OCH$_2$CH$_2$OCH$_3$, —(OCH$_2$CH$_2$)$_2$OCH$_3$, —(OCH$_2$CH$_2$)$_3$OCH$_3$, —SCH$_3$, —S(O)CH$_3$, —SC$_6$H$_5$, —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), —NHC(O)CH$_3$, and the like. Moreover, each Ar, X, D and T group may contain one or more such substituent groups which may also be the same or different in any given ligand molecule. Preferred substituent radicals include alkyl and alkoxy radicals containing from 1 to 18 carbon atoms and more preferably from 1 to 10 carbon atoms, especially t-butyl and methoxy.

Further in rhodium catalyzed hydroformylation reactions, substitution (excluding the bridging group —(CH$_2$)$_y$—(Q)$_n$—(CH$_2$)$_y$— when present) at the ortho positions of the aryl groups of the Ar, X, D and T groups of the above formulae relative to the oxygen atom that bonds each aryl group to a phosphorus atom of the ionic phosphite ligand, may influence the catalytic activity and/or stability of the ligand due to steric hindrance around the phosphorus atom of the ionic phosphite ligand caused by substitution in such ortho positions. For example, too much steric hindrance may affect the ability of the ionic phosphite ligand to bond to the Group VIII metal (e.g. rhodium), while not enough steric hindrance may cause the ionic phosphite to bond too strongly.

One class of preferred ligands of the above formulae are those designated as I-A, II-A and III-A above, wherein both $Y^1$ and $Y^2$ are radicals having a steric hindrance of at least isopropyl or greater such as branched chain alkyl radicals having three to five carbon atoms, especially t-butyl, while more preferably $Z^2$ and $Z^3$ are both alkoxy radicals, especially methoxy.

Accordingly further preferred classes of ionic phosphite ligands employable in this invention are those of the formulae

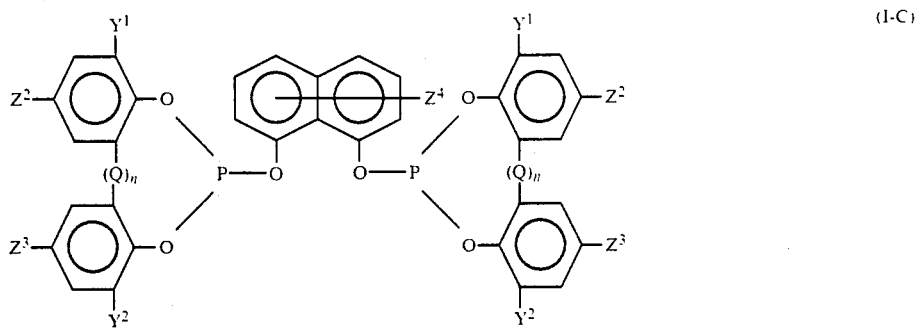
(I-C)
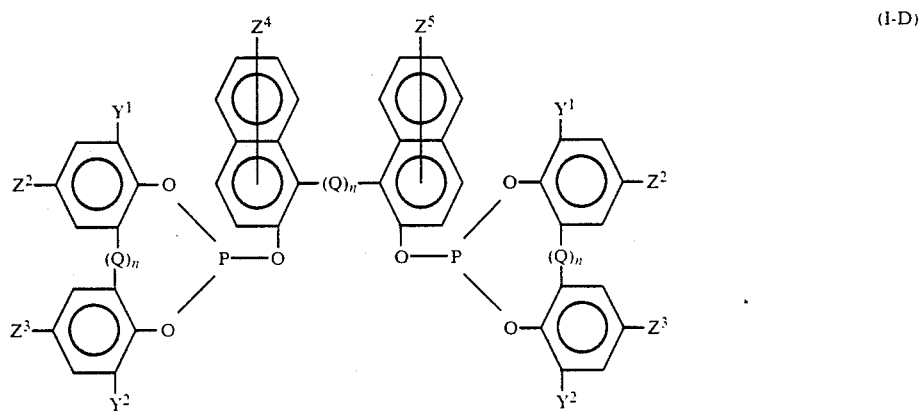
(I-D)
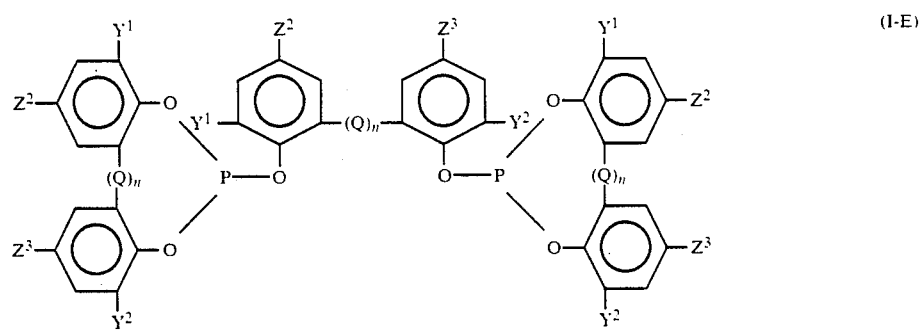
(I-E)
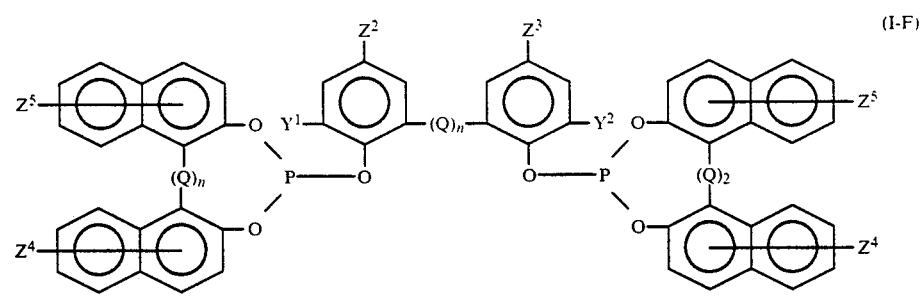
(I-F)
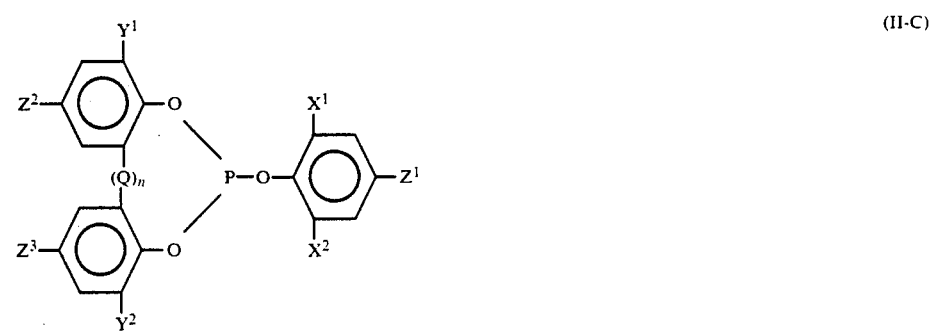
(II-C)

-continued
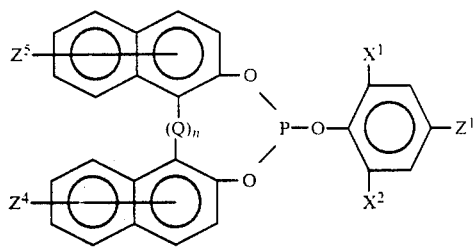
(II-D)
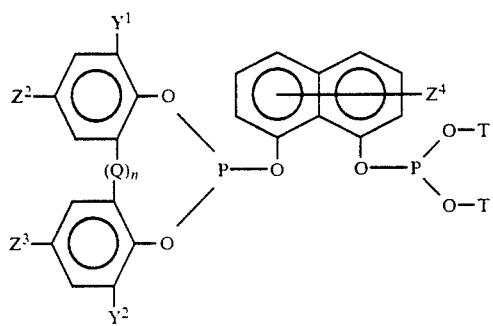
(III-C)
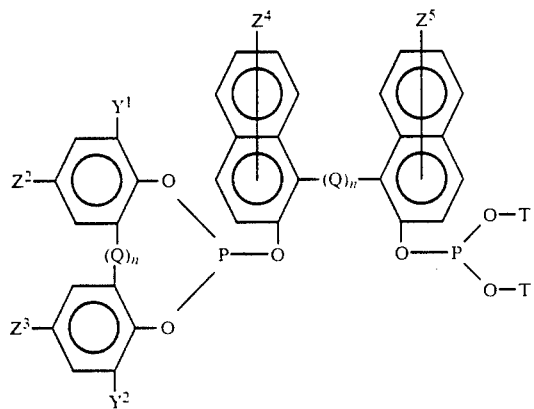
(III-D)
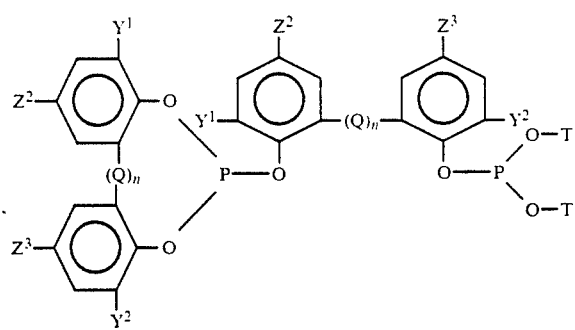
(III-E)
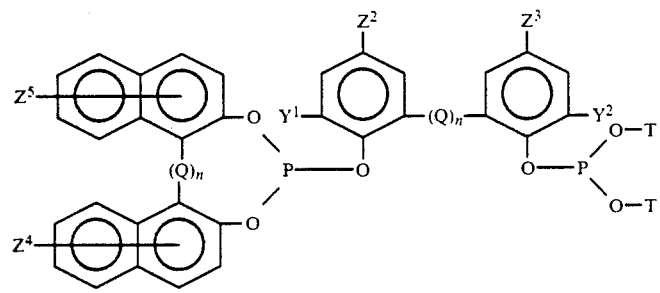
(III-F)

wherein $Y^1$, $Y^2$, $Z^2$, $Z^3$, $Z^4$, $Z^5$, Q, n and T in the above formulae are the same as herein generically and preferably defined above.

Illustrative ionic phosphite salt ligands include those having the following general formulae, wherein

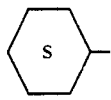

represents a cyclohexyl radical;
$CO_2$ represents a carboxyl group

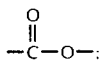

tBu represents a tertiary butyl radical; and
$C_9H_{19}$ represents branched mixed nonyl radicals.

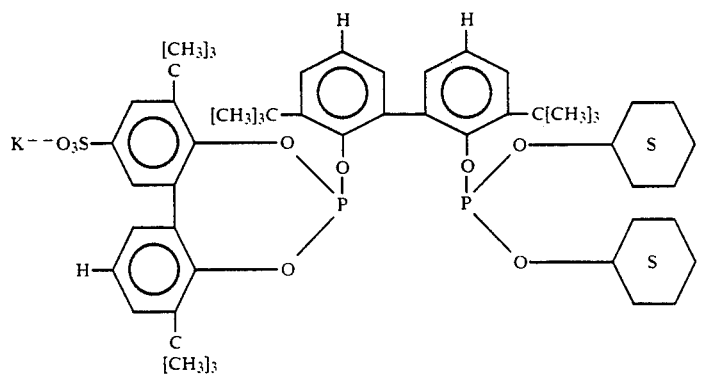

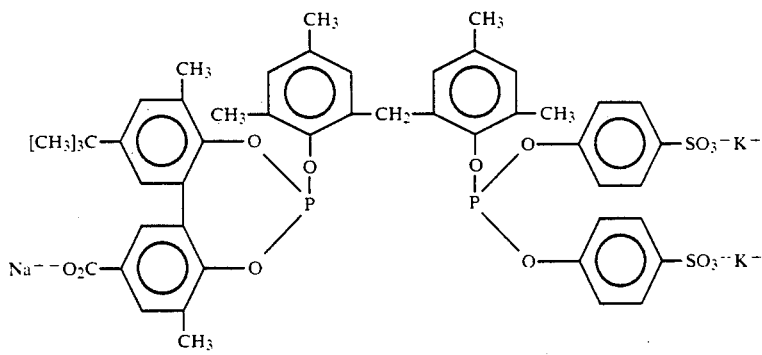

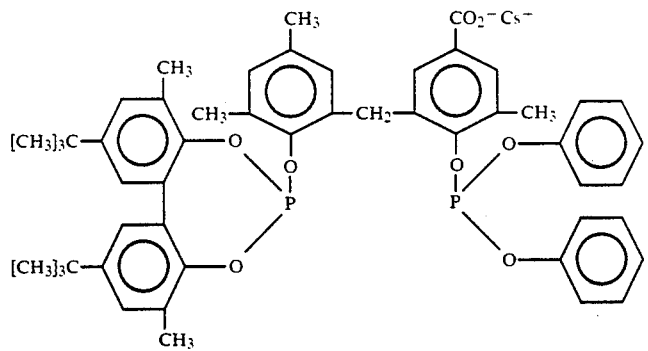

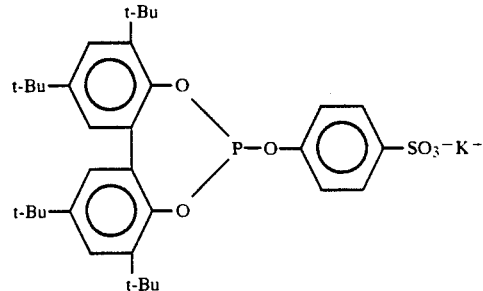

-continued
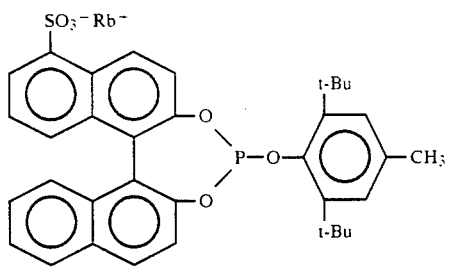
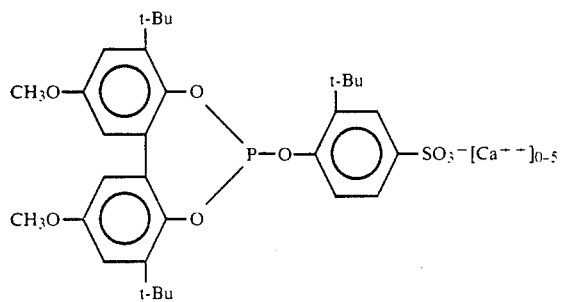
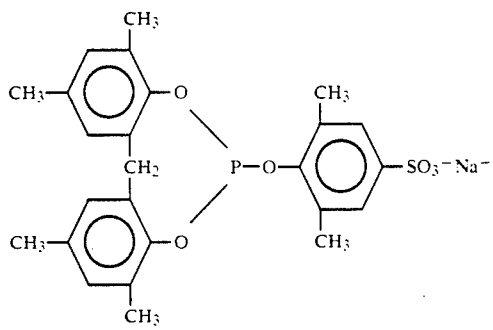
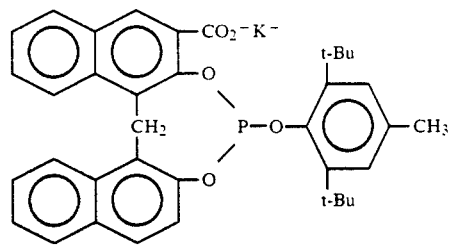
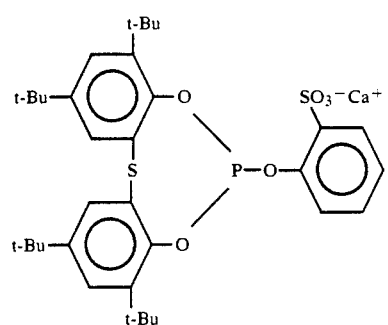

-continued
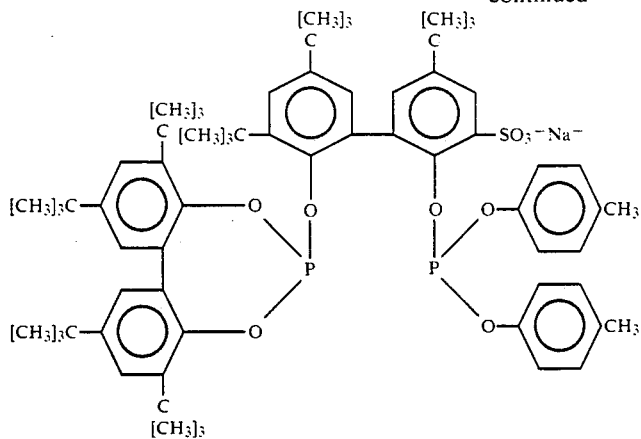
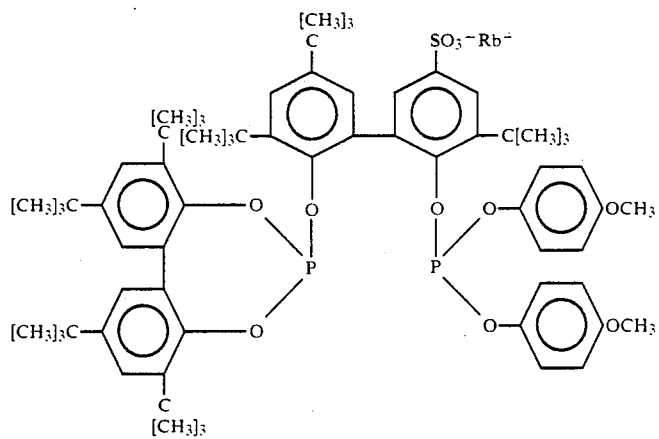
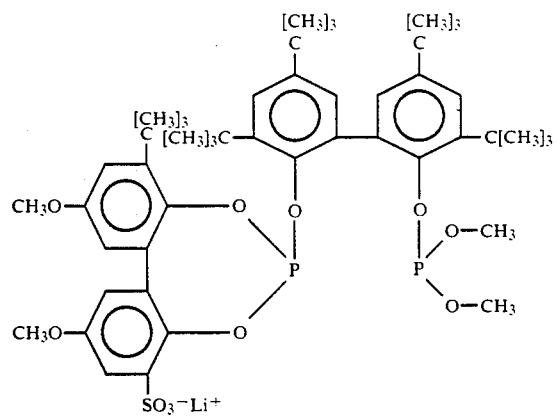
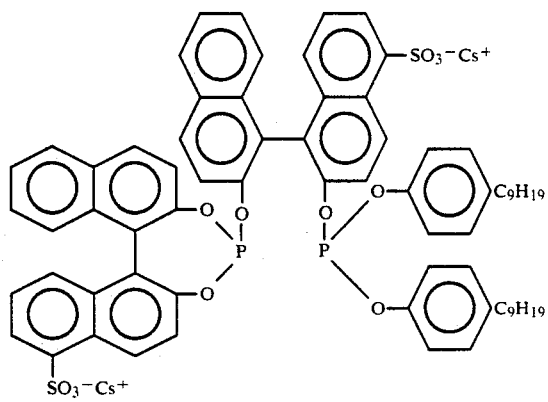

-continued
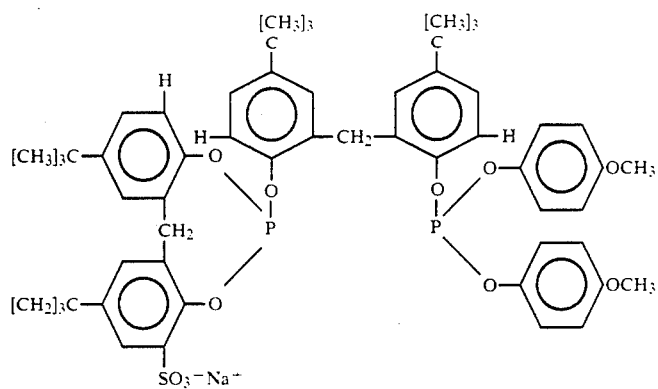
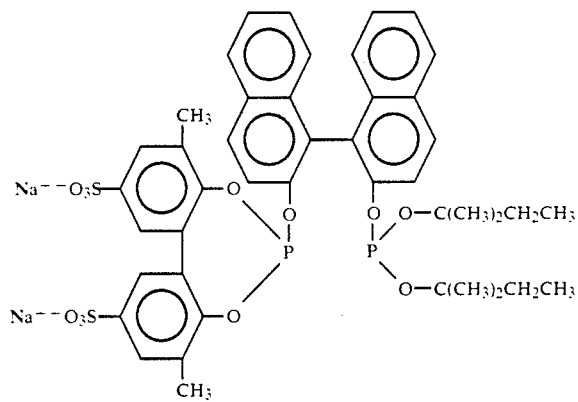
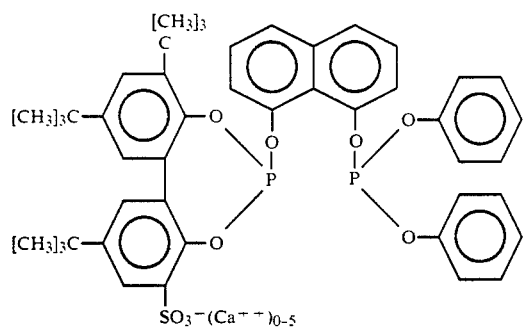
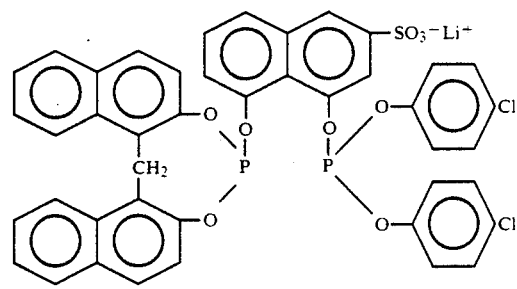

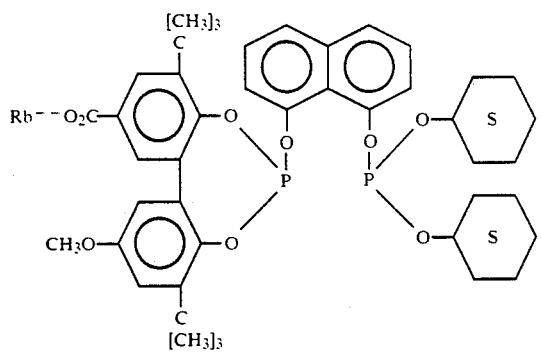
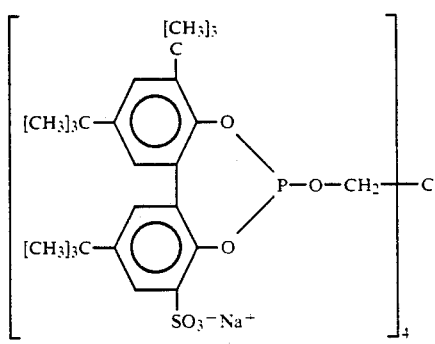
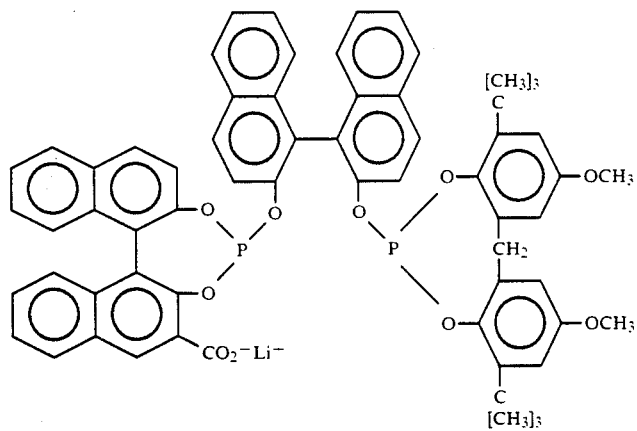
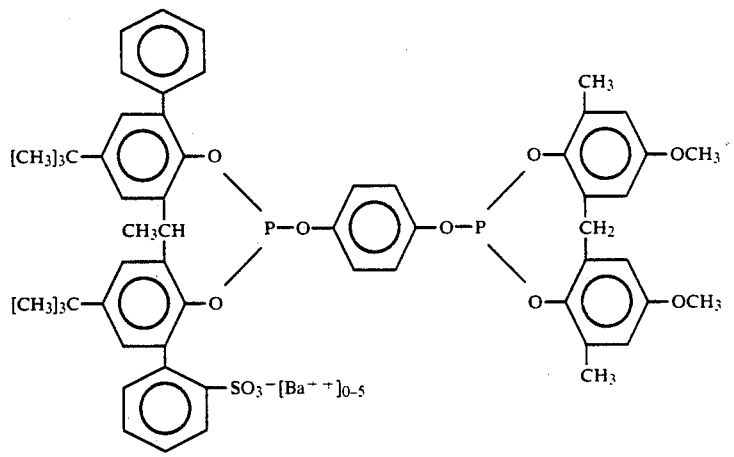

-continued
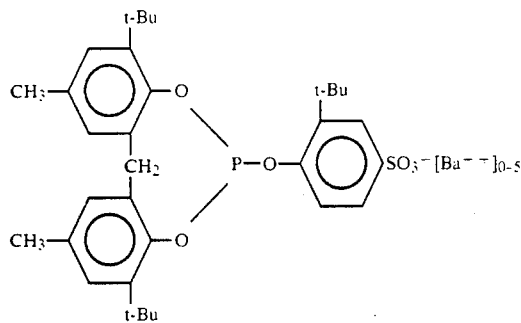
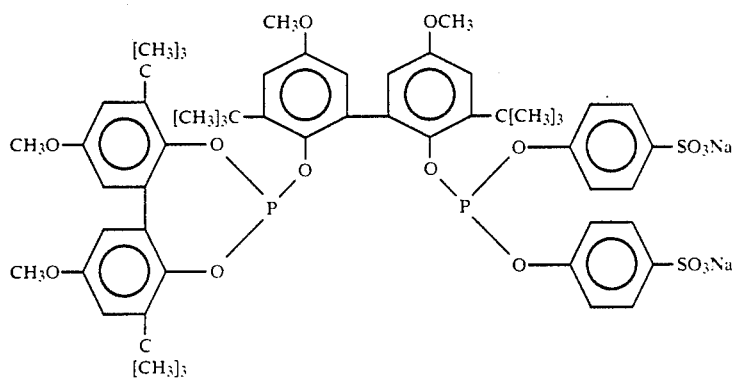
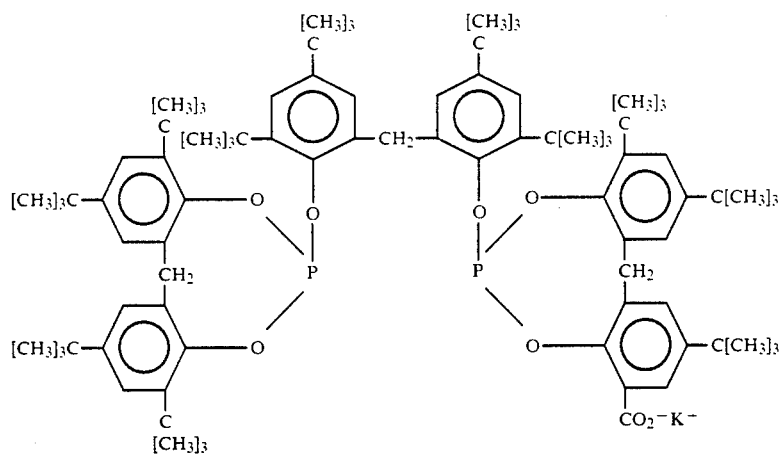
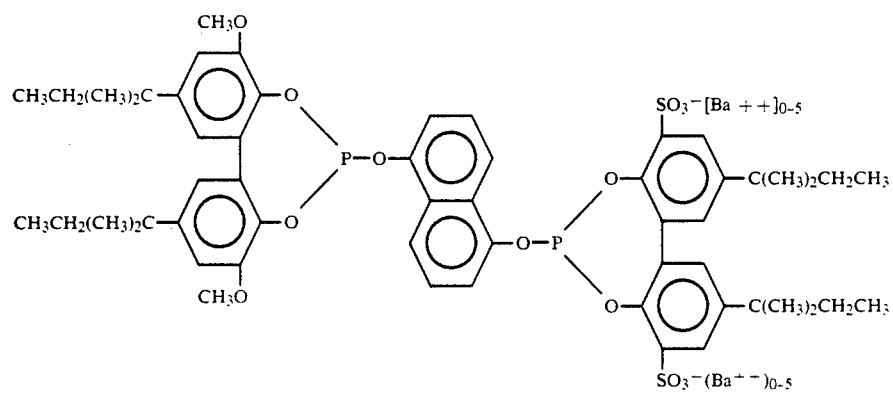

-continued
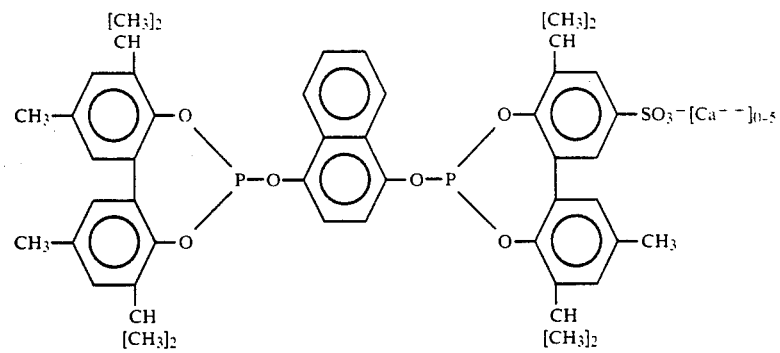
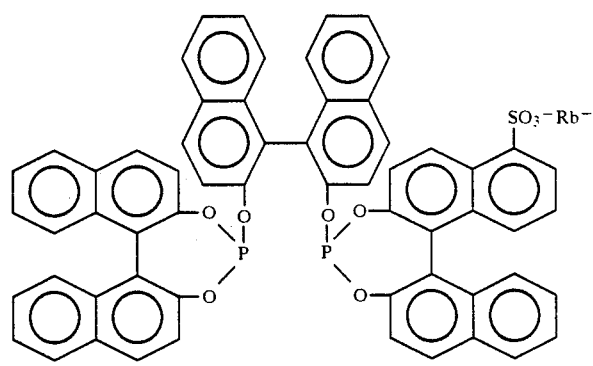
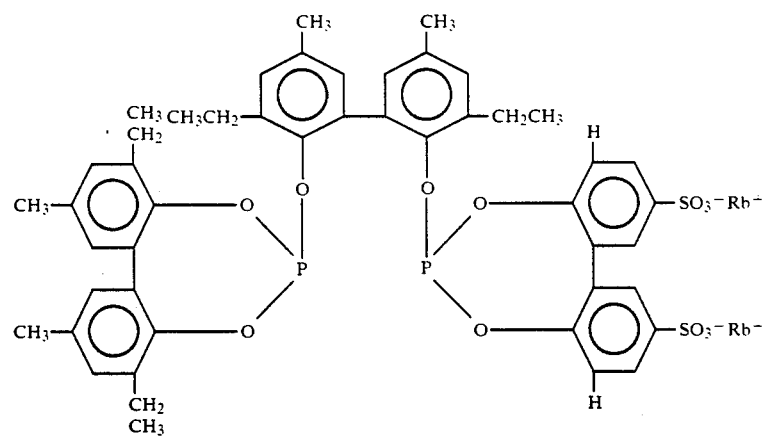
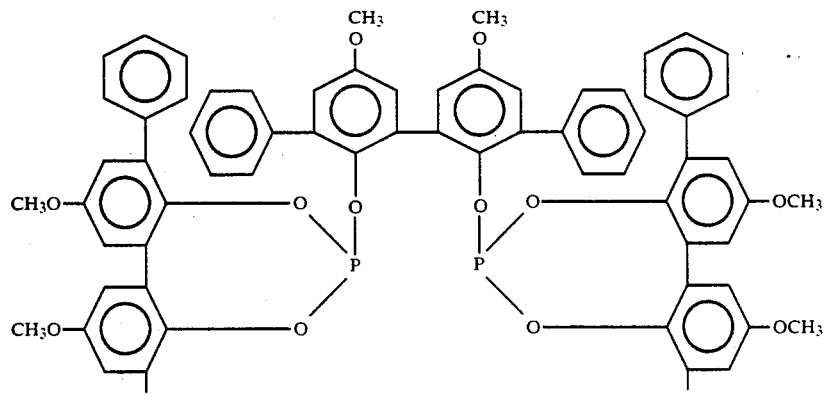

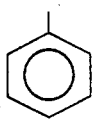

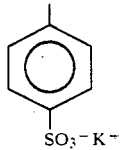

The ionic phosphite ligands employable in this invention can be readily prepared via a series of conventional phosphorus halide-alcohol condensation reactions. Such types of condensation reactions and the manner in which they may be conducted are known in the art as seen for example by U.S. Pat. Nos. 4,599,206 and 4,717,775 directed to nonionic type diorganophosphite ligands of Formula (II) above; U.S. Pat. No. 4,748,261 directed to nonionic type open-ended, bis-phosphite ligands of Formula (III) above; and U.S. Pat. No. 4,668,651 directed to nonionic type poly-phosphite ligands of Formula (I) above. For instance, the method for preparing ionic diorganophosphite ligands of Formula (II) above can comprise reacting a corresponding organic diol (dihydroxy) compound with phosphorus trichloride to form an organic phosphorochloridite intermediate which in turn is reacted with a corresponding organic mono-ol (monohydroxy) compound to produce the desired ionic diorganophosphite ligand. Optionally such ligands can be prepared in reverse order, for instance, from a corresponding organic phosphorochloridite and a corresponding diol compound. Likewise ionic open-ended bis-phosphite ligands of Formula (III) above can be prepared by (a) reacting a corresponding organic dihydroxy compound with phosphorus trichloride to form a corresponding organic phosphorochloridite intermediate, (b) reacting said intermediate with an organic diol (corresponding to D in Formula (III) above) to form a corresponding hydroxy substituted diorganophosphite intermediate, (c) reacting said hydroxy substituted diorganophosphite intermediate with phosphorus trichloride to form the corresponding organic phosphorodichloridite intermediate and (d) reacting said dichloridite with two moles of a corresponding organic mono-ol compound (or one mole each of two different mono-ols) to arrive at the corresponding desired ionic, open-ended bis-phosphite ligand. Such condensation reactions may also be carried out in a single-pot synthesis, if desired. Further ionic poly-phosphite ligands of Formula (I) above can be prepared by the same type of phosphorus halide-alcohol condensation reactions as noted above for preparing the ionic ligands of Formula (III) above, for instance, employing, e.g. a diol in step (b) above corresponding to X in Formula (I) and reacting the dichloridite intermediate of step (d) above with a corresponding diol instead of two moles of a mono-ol, to produce the desired ionic poly-phosphite ligand. Alternatively such ionic polyphosphites could be prepared by a single-pot synthesis, e.g. by reacting the corresponding organic phosphorochloridite intermediate of step (a) above or a mixture of different corresponding chloridite intermediates with a polyol corresponding to X, the mole amount of chloridite employed being equal to the number of hydroxy groups on the polyol employed. For example two mole equivalents of the same phosphorochloridite intermediate of step (a) above (or one mole each of two different such intermediates) could be reacted with one mole equivalent of a diol corresponding to X to form a close-ended bis-phosphite type ligand as shown e.g. by Formulae (I-C) to (I-F) above.

Moreover, since the ionic phosphite ligands as defined in this invention must contain at least one ionic moiety selected from the group consisting of salts of sulfonic acid and of carboxylic acid substituted on an aryl radical, it is preferred that at least one of the organic reactants or intermediates of the halide-alcohol condensation reactions employable in preparing such ionic ligands contain at least one such ionic moiety substituted on an aryl moiety, though it may be possible to provide such ionic moieties after the production of a nonionic phosphite ligand by conventional sulfonation or carboxylation techniques. Salts of sulfonated and carboxylated acids of simple hydroxy compounds, such as phenolic and naphtholic mono-ols and diols, and/or methods for their preparation are known.

Moreover, while such phosphorus halide-alcohol condensation reactions may be carried out in the presence of a solvent e.g. toluene and a HCl acceptor e.g. an amine, it is a preferred to employ double salts of ionic mono-ol reactants and triple salts of ionic diol reactants in the presence of a dipolar aprotic solvent such as N-methyl pyrolidone (NMP), dimethyl sulfoxide (DMSO), dimethyl formamide (DMF), sulfolane, and the like, when such ionic type reactants are condensed with a desired phosphorus-halide containing moiety e.g. PCl$_3$, phosphorochloridite or phosphorodichloridite compound in order to avoid the need for any HCl acceptor. Such double or triple salts and/or methods for their preparation are well known.

For example, one starting material could be the double salt of phenol p-sulfonic acid or the double salt of hydroxy p-benzoic acid, depending upon whether the sulfonate or carboxylate form of the ionic phosphite is desired. Other suitable starting materials will be obvious to those skilled in the art and these materials may be substituted or unsubstituted at other sites on the benzene ring. The double salt (phenolate sulfonate or phenolate carboxylate) can be prepared by addition of suitable basic material, such as sodium hydroxide or potassium hydroxide, to the corresponding starting mono-ol material. Formation of the double salt conveniently can be carried out in a solution of starting material and base in aprotic solvent and water. The water may be provided by an aqueous solution of the base.

The water then is removed from the solution of the double salt e.g. by azeotropic distillation with toluene. For example, a sufficient quantity of toluene is thoroughly mixed with the solution containing the double salt, to form a toluene/water azeotrope having boiling point of about 85° C. at atmospheric pressure. The azeotropic composition contains about 80% toluene and 20% water. The aprotic solvent and the double salt have a low volatility at these conditions, and so are easily separated from the toluene/water azeotrope.

Because the double salt is essentially insoluble in aprotic solvent, a suspension of double salt in aprotic solvent forms as the azeotropic composition is removed.

This suspension then is reacted with the halide compound of a desired phosphorus-containing moiety, i.e., with an organic phosphorochloridite or phosphorodichloridite. The chlorine atom of the phosphorus-containing moiety reacts readily with the cation of the hydroxy group of the double salt to yield the desired ionic phosphite. By-product cation/halide salt is not soluble in the aprotic solvent, and can be removed by filtration or any soluble solid/liquid separation technique known in the art, e.g., filtration.

The ionic phosphite composition can be easily separated from the aprotic solvent, e.g. by removing the aprotic solvent from the mixture under vacuum distillation conditions. The thus recovered ionic phosphite material can be further purified by recrystallization in ways known to those skilled in the art and the purified ionic phosphite material utilized in this invention. Other ionic phosphites employable in this invention can be readily prepared by those skilled in the art employing similar techniques.

Ionic phosphite ligands and Group VIII transition metal-ionic phosphite ligand complex catalysts of this invention may not be sufficiently soluble in non-aqueous hydroformylation reaction media which also contain olefin, aldehyde product, and higher boiling condensed aldehyde by-products to obviate use of a solubilizing agent. Thus, an organic solubilizing agent or co-solvent compatible with all constituents may be employed to solubilize ionic phosphite.

Suitable organic solubilizing agents include those selected from the group consisting of an alkylene oxide oligomer having an average molecular weight of at least 150, an organic nonionic surfactant mono-ol having an average molecular weight of at least 300, a polar organic compound having a molecular weight of less than 150 and a Hildebrand solubility value of at least 10, and mixtures thereof.

While not intending to be bound by any precise explanation of exactly how these solubilizing agents actually work in rendering ionic-phosphite ligands and Group VIII transition metal-ionic phosphite ligand complex catalysts soluble in non-aqueous hydroformylation reaction media, it is submitted that the solubilizing agents, which are themselves readily soluble in the non-aqueous hydroformylation reaction media, may be viewed as encapsulating the ligand and complex catalyst, thus rendering them soluble in the non-aqueous hydroformylation reaction media. Alternatively, the solubilizing agents may be viewed as coordinating with the ligand salt to form a complex which is soluble in the non-aqueous hydroformylation reaction medium thus also rendering the complex catalyst derived therefrom soluble in said reaction medium.

In any event, the subject invention is not predicated on knowing exactly how the added solubilizing agent actually renders the generally insoluble ligands and catalysts soluble in non-aqueous hydroformylation reaction media. Rather it is sufficient for the purpose of this invention to understand that when the hydroformylation reaction media also contain organic solubilizing agent, the ligands and complex catalysts derived therefrom are rendered soluble in said hydroformylation reaction media.

The alkylene oxide oligomers employable in this invention are liquids or low melting solids, which become liquid at the hydroformylation process reaction temperature, having an average molecular weight of at least about 150, and preferably in the range of from about 150 to about 10,000, and include such oligomers as aliphatic polyalkylene oxide polyols and cyclic polyalkylene oxide ethers. More preferably, such oligomers are those having an average molecular weight in the range of from about 500 to about 7,000, and most preferably from about 500 to about 2,000. Such compounds and methods for their preparation are well known. Such aliphatic polyalkylene oxide polyols include poly(oxyalkylene) glycols, polyalkylene oxide derivatives of glycerine (also commonly referred to as polyether triols), as well as polyether polyols having a functionality of greater than three, and the like. Such alcohols are readily available to the public under such trade names as CARBOWAX® PEG, CARBOWAX® TPEG, NIAX® PPG and UCON® fluids (all products of Union Carbide Corporation), as well as POLYGLYCOL-E® (Dow Chemical Co.) POLY-G® (Olin Corp.), PLURACOL-E® (BASF-Wyandotte Corp.), JEFFOX® (Texaco Inc.) and the like.

Preferred poly(oxyalkylene) glycols include those represented by the following formula and mixtures thereof:

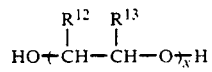

wherein x represents an integer, and $R^{12}$ and $R^{13}$ are selected from the group consisting of hydrogen and methyl radicals. Of course, each $R^{12}$ and $R^{13}$ group in a given compound may be the same or different. More preferably, the poly(oxyalkylene) glycols are selected from the group consisting of poly(oxyethylene) glycols, poly(oxypropylene) glycols, and mixtures thereof. Illustrative poly(oxyalkylene) glycols include CARBOWAX® PEG-600, a poly(oxyethylene) glycol having an average molecular weight of about 600, CARBOWAX® PEG-150, a poly(oxyethylene) glycol having an average molecular weight of about 150, NIAX® PPG-1025, a poly(oxypropylene) glycol having an average molecular weight of 1025, and the like.

Illustrative preferred polyalkylene oxide derivatives of glycerine include these represented by the following formula and mixtures thereof:

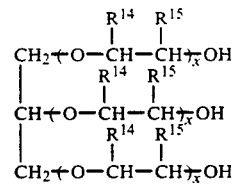

wherein x represents an integer, and $R^{14}$ and $R^{15}$ are selected from the group consisting of hydrogen and methyl radicals. Of course, each $R^{14}$ and $R^{15}$ group in a given compound may be the same or different. More preferably, the polyalkylene oxide derivatives of glycerine are polyethylene oxide derivatives of glycerine, such as CARBOWAX® TPEG-990, a polyethylene oxide derivative of glycerine having an average molecular weight of about 990.

Illustrative cyclic polyalkylene oxide ethers employable in this invention include the crown ethers described in U.S. Pat. No. 4,162,261. Crown ethers and methods for their manufacture are well known. Crown ethers employable herein consist essentially of carbon, hydrogen, and oxygen and may be termed monocyclic or polycyclic. Minor amounts of ether atoms which do not appreciably contribute to the solvency function of the crown ether according to this invention may also be present. In general, crown ethers contain in the principal ring at least 4 oxygen atoms, each separated from the other by at least two aliphatic carbon atoms in series. Preferably, the principal ring contains at least two ring oxygen atoms which are each joined to ethylene or substituted ethylene groups. The remainder of the principal ring oxygen atoms are joined to either trimethylene, tetramethylene, substituted trimethylene, or substituted tetramethylene groups, or mixtures thereof. Schematic characterizations of such crown ethers, as well as a more detailed description of such crown ethers, can be found in U.S. Pat. No. 4,162,261, the entire disclosure of which is incorporated herein by reference thereto. Preferred crown ethers contain fewer than about 50 ether oxygen atoms in the principal ring and more preferably contain from 4 to 15 ether oxygen atoms in the principal ring. Moreover, because of their ease of manufacture, monocyclic crown ethers are most preferred. Illustrative specific crown ethers include 15-crown-5 and 18-crown-6, and the like, such as shown and described in U.S. Pat. No. 4,162,261.

The organic nonionic surfactant mono-ols employable in this invention are liquids having an average molecular weight greater than about 300, preferably in the range of from about 300 to about 5,000, more preferably having an average molecular weight in the range of from about 500 to about 2,000, and include such surfactants as alcohol alkoxylates. Such compounds as well as methods for their preparation are well known, as in U.S. Pat. No. 4,453,022, the entire disclosure of which is incorporated herein by reference thereto. Such alcohol alkoxylates are the reaction products of a monohydroxy alkyl compound or alkyl substituted phenol, wherein said alkyl radicals may contain from 4 to 25 carbon atoms, with an alkylene oxide. Of course it is to be understood that such monohydroxy alkyl compounds, in addition to individual mono-ols, may be mixtures of aliphatic mono-ols such as those derived by conventionally known methods from petroleum compounds or natural fats and oils. Illustrative alcohol alkoxylates include those represented by the following formula and mixtures thereof:

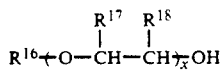

wherein x represents an integer, $R^{16}$ represents a radical selected from the group consisting of aliphatic primary, secondary and branched alkyl radicals, alkylphenyl radicals, and mixtures thereof, and $R^{17}$ and $R^{18}$ are selected from the group consisting of hydrogen and methyl radicals. Of course, each $R^{17}$ and $R^{18}$ in a given alkoxylate may be the same or different. More preferably, each $R^{17}$ and $R^{18}$ group represents hydrogen, the more preferred alcohol alkoxylates being alcohol ethoxylates.

The alcohol alkoxylates employable in this invention contain both water-soluble (polar) and oil-soluble (nonpolar) groups and are readily available to the public under such trade names as TERGITOLS® (Union Carbide Corporation), IGEPALS® (GAF Corp.), ALFONICS® (Conoco Inc.), BRIJ® (ICI), NEODOLS® (Shell Chemical Co.), STANDAMULS® (Henkel Corp.), SURFONICS® (Texaco Chemical Co.), TRITONS® (Rohm & Haas Co.), and the like, such as disclosed, for example in U.S. Pat. No. 4,453,022 and Kirk-Othmer's "Encyclopedia of Chemical Technology", Third Edition, Vol. 22, pp. 338–339 and 364–366 (1983). Among the more preferred alcohol alkoxylates are TERGITOLS® such as those represented by the general alcohol ethoxylate formula

wherein $R^{16}$ and x are the same as defined above. The identity of a variety of such products is described in the following TABLE.

TABLE

| Trade Name | $R^{16}$ | $x_{Avg}$ |
|---|---|---|
| TERGITOL® 25-L-5 | $C_{12}-C_{15}{}^a$ | 5 |
| TERGITOL® 26-L-5 | $C_{12}-C_{16}{}^a$ | 5 |
| TERGITOL® 15-S-3 | $C_{11}-C_{15}{}^b$ | 3 |
| TERGITOL® 15-S-7 | $C_{11}-C_{15}{}^b$ | 7 |
| TERGITOL® NP-4 | nonylphenyl$^c$ | 4 |
| TERGITOL® NP-9 | nonylphenyl$^c$ | 9 |
| TERGITOL® 24-L-15N | $C_{12}-C_{14}{}^a$ | 4.8 |
| TERGITOL® 24-L-50N | $C_{12}-C_{14}{}^a$ | 6.5 |
| TERGITOL® 24-L-75N | $C_{12}-C_{14}{}^a$ | 8.0 |

$^a$Linear-primary alkyls
$^b$Linear-secondary alkyls
$^c$Branched nonyl

The polar organic compounds that may also be employed as the organic solubilizing agent of this invention include organic liquids having a molecular weight of less than 150 and a Hildebrand solubility value of 10 or higher, and mixtures thereof. Illustrative examples of such polar compounds (along with their Hildebrand solubility parameters) include lower alcohols e.g., methanol (12.9), ethanol (11.2), propanol (10.2), isopropanol (10.2) and the like; nitriles e.g., benzonitrile (10.7), acetonitrile (11.8), propionitrile, and the like; N,N-disubstituted amides e.g., dimethylformamide (11.5), dimethylacetamide, N-alkylpyrrolidones, such as N-methylpyrrolidone (14.8), and the like; sulfoxides e.g., dimethyl sulfoxide (12.8) and the like; and sulfones e.g., dimethyl sulfone, sulfolane, and the like. Hildebrand solubility values are an empirical measure of the relative polarity of an organic compound and are described, e.g., in "Introduction to Modern Liquid Chromatography" by L. R. Snyder and J. J. Kirkland, pp. 215–218 (1974) a Wiley-Interscience publication, (John Wiley & Sons) and the "The Solubility of Non-Electrolytes", J. H. Hildebrand and R. L. Scott, pp. 424–434, Dover Publications Inc., New York (1964).

As described above, there are three different compound classes or organic solubilizing agents, i.e., (a) alkylene oxide oligomers, (b) organic nonionic surfactant mono-ols, and (c) organic polar compounds, that may be employed in this invention. Moreover, each compound class may be employed individually (i.e. one or more different solubilizing agents of the same compound class), or mixtures of two or more different compound classes (i.e. one or more different solubilizing agents from the same compound class along with one or more different solubilizing agents from one or both of the other two different compound classes) may be employed in any hydroformylation process of this invention. Of course, the total amount of organic solubilizing agent present in the non-aqueous hydroformylation reaction medium of a given process need only be that minimum amount necessary to render the ionic phosphite ligand and complex catalyst derived therefrom soluble in the non-aqueous hydroformylation reaction medium, without regard to whether solvent is selected from one or more compound classes. In general, it is considered preferable to employ an excess beyond the minimum required, although no added benefit is seen in employing large excess amounts.

Accordingly when employed, either as an individual compound class or as part of a mixture of different compound classes, the alkylene oxide oligomer solubilizing agents of this invention may be employed in amounts ranging for about 1 to about 35 weight percent of the non-aqueous hydroformylation reaction medium (amounts ranging from about 1 to 30 weight percent being preferred), organic nonionic surfactant mono-ol solubilizing agents of this invention may be employed in amounts ranging from about 1 to about 60 weight percent of the non-aqueous hydroformylation reaction medium (amounts ranging from about 1 to 50 weight percent being preferred), and the organic polar compound solubilizing agents of this invention may be employed in amounts ranging from about 1 to 60 weight percent of the non-aqueous hydroformylation reaction medium (amounts ranging from 1 to about 35 weight percent being preferred); with the proviso that, when a mixture of two or more different compound classes of such solubilizing agents is employed, the total amount of the sum of such solubilizing agents of said mixture employed is not greater than about 60 weight percent of the non-aqueous hydroformylation reaction medium, and preferably is not greater than about 50 weight percent of the non-aqueous hydroformylation reaction medium.

The above-described maxima pertain to the amount of solubilizing agent present in the hydroformylation reaction medium of the process and not to that amount which might be present in a liquid recycle medium of a continuous process, said recycle medium having been concentrated, e.g. by removal and recovery of some of the desired aldehyde product. Likewise, it is to be understood that additional amounts of solubilizing agent may be added during the process when and if desired, to maintain the desired quantity of solubilizing agent throughout the process, e.g. when additional ligand and/or catalyst is added to the process, provided that the above maximum quantities of the various solubilizing agents and mixtures thereof are not exceeded. Further the manner and order of addition of solubilizing agent to the non-aqueous hydroformylation reaction medium is not critical, although it is generally preferred to employ same along with the ligand and complex catalyst right from the start of the process.

Ionic phosphite ligands and their corresponding Group VIII transition metal-ionic phosphite ligand complex catalysts may be sufficiently soluble in low molecular weight aldehydes (i.e., $C_3$ to $C_6$), so as to be directly employable in such non-aqueous hydroformylation reactions without the need for solubilizing agent. The molecular weight of the aldehyde product has a direct bearing on the solubilization of ionic phosphite ligands and corresponding Group VIII transition metal-ionic phosphite complex catalysts. Polarity of aldehydes, which effects the solubility in the aldehyde of ligands and their corresponding complex catalysts, decreases as aldehyde molecular weight increases. Thus, lower molecular weight aldehydes ($C_3$ to $C_6$) are more polar than high molecular weight aldehydes (e.g. $C_7$ and heavier). For example, butyraldehyde is significantly more polar than nonanal, and thus ligand and complex catalyst is more easily solubilized in butyraldehyde.

Alkylene oxide oligomers described above are useful as solubilizing agents of this invention. However, oligomer polyol-salt solutions tend to become very polar at high ligand concentration and may form a separate transparent liquid layer (i.e. a second organic phase) with non-polar aldehydes such as nonanal. Thus, if one wishes to maintain a one-phase, homogeneous solution in such instances, one may include an additional solubilizing agent or mixtures thereof selected from the group consisting of the organic non-ionic surfactant mono-ols and the polar organic compounds, as described above, along with the alkylene oxide oligomer polyol.

Solutions of the ionic phosphite ligands in the organic nonionic surfactant mono-ols employable in this invention, in general, mix readily and totally evenly with non-polar aldehydes (e.g., nonanal), thus providing significantly higher ionic phosphite solubilities than alkylene oxide oligomers. Further, the nonionic surfactant mono-ols work synergistically with the alkylene oxide oligomers and, when employed together, may solubilize more ligand and achieve higher ligand concentration than can be achieved with either class of compounds used alone.

The aforementioned alkylene oxide oligomers and nonionic surfactant mono-ols are relatively non-volatile. However, one drawback in the utilization of the polar organic compounds is their high volatility. Such high volatility may cause the polar organic compound to be stripped during catalyst-aldehyde product separation and may also cause ligand catalyst precipitation. Thus, when used alone in a continuous operation, the amount of polar organic compound employed should be carefully monitored and maintained during operation. However, when used in conjunction with the non-volatile alkylene oxide oligomers and/or non-volatile nonionic surfactant mono-ols, said polar organic compounds may greatly enhance the ligand solubility in mixtures of olefins and polar or non-polar aldehydes.

The alkylene oxide oligomers and organic nonionic surfactant mono-ols employable in this invention and described above comprise the condensation products of an alkylene oxide, such as ethylene oxide or propylene oxide, or mixtures of ethylene oxide or propylene oxide, with ethylene glycol (or glyerine) in the case of the alkylene oxide oligomers, or an alcohol in the case of the nonionic surfactant mono-ols. Conventional preparative procedures generally yield a mixture of condensation species of different molecular weight containing a number of glycol, glycerine, or alcohol derivatives having different molecular proportions of alkylene oxide. Thus, the product compounds obtained are, in reality, a mixture of derivatives of the glycol, glycerine, or alcohol moiety containing different molecular portions of alkylene oxide units. Moreover in the case of alcohol alkoxylates, the alcohol moiety itself may be derived from one or more alcohols, e.g., a mixture of alcohols, such as $C_{11}$ to $C_{15}$ alkyl alcohols. Thus as is well known the conventional designation of the number of alkylene oxide units (x in the above alkylene oxide oligomer polyol and alcohol alkoxylate formulae) present in a molecule of alkylene oxide oligomer or alcohol alkoxylate is a designation of the average number of alkylene oxide units per molecule and that a substantial proportion of the alkylene oxide oligomer or alcohol alkoxylate has a greater number and a substantial proportion has a lesser number of alkylene oxide units present than the average value, x, would indicate. Such designations of such products are well understood in the art and are employed herein consistent with their well understood meanings.

The Group VIII transition metals which make up the metal-ionic phosphite ligand complexes of this invention include those selected from the group consisting of rhodium (Rh), cobalt (Co), iridium (Ir), ruthenium (Ru), iron (Fe), nickel (Ni), palladium (Pd), platinum (Pt), osmium (Os), and mixtures thereof. For hydroformylation processes, the preferred metals are Rh, Co, Ir, and Ru; more preferably, Rh, and Co, and most preferably Rh.

Successful practice of this invention does not depend and is not predicated on the exact structure of the catalytically active metal complex species, which may be present in mononuclear, dinuclear, and polynuclear forms. Indeed, the exact active structure is not known. Although the inventors do not wish to be bound by any theory, it appears that the active catalytic species may, in its simplest form, consist essentially of the Group VIII transition metal in complex combination with carbon monoxide (present for hydroformylation processes) and ionic phosphite salt ligand.

The term "complex" as used herein and in the claims means a coordination compound formed by the union of one or more electronically rich molecules or atoms capable of independent existence with one or more electronically poor molecules or atoms, each of which is also capable of independent existence. Carbon monoxide (which is also properly classified as a ligand) may be present and can be complexed with the Group VIII transition metal. The ultimate composition of the active complex catalyst may also contain an additional organic ligand or anion which satisfies the coordination sites or nuclear charge of the Group VIII transition metal-organophosphite catalyst, such as hydrogen and the like. It is of course to be understood that the active complex species preferably is free of any additional organic ligand or anion that might poison the catalyst and have an undue adverse effect on catalyst performance. For instance, it is known that halogen anions can poison conventional rhodium catalyzed hydroformylation catalysts. Accordingly, it is preferred that the active catalysts of this invention be free of halogen directly bonded to rhodium.

The number of available coordination sites on such Group VIII transition metals is well-known in the art and ranges from 4 to 6. By way of illustration, it appears that the preferred active rhodium hydroformylation catalyst species of this invention contains, in its simplest form, an amount of ionic phosphite ligand and carbon monoxide equal to a total of four mols in complex combination with one mol of rhodium. Thus, the active species may comprise a complex catalyst mixture, in mononuclear, dinuclear, or polynuclear forms, which are characterized by one, two, and/or three ionic phosphite salt molecules complexed per one molecule of rhodium. As noted above, carbon monoxide is also present and complexed with the rhodium in the active species of hydroformylation catalyst.

Moreover, the active species of the preferred rhodium hydroformylation catalyst may also be complexed with hydrogen in addition to the ionic phosphite salt and carbon monoxide ligands. Indeed, it is believed that the active species of any Group VIII transition metal catalyst of this invention may also contain hydrogen, in addition to the ionic phosphite and carbon monoxide ligands, during hydroformylation, particularly in view of the hydrogen gas employed in the process.

Further, whether one preforms the active complex catalyst prior to introducing it into the hydroformylation reaction zone or the active species is prepared in situ during hydroformylation, the hydroformylation reaction is carried out in the presence of free ionic phosphite ligand. For example, the ultimate composition of the preferred active rhodium complex species catalyst is the result of competing reactions between carbon monoxide and ionic phosphite ligands for complexing or coordination sites on the rhodium molecule. These competing reactions can be controlled by adjusting the concentration of the ionic phosphite ligand in the reaction medium.

Generally, the stronger ligand (carbon monoxide or ionic phosphite) will occupy a major portion of the coordination or complexing sites. For example, one may view the function of free ionic phosphite ligand either as maintaining the status quo of the various forms of active complex catalyst during the hydroformylation, or as shifting the equilibrium of the competing reactions in its favor. This shift causes additional ionic phosphite ligands to enter into complex combination with rhodium, probably by displacing a similar number of carbon monoxide ligands from the complex catalyst.

The ionic phosphite ligands of this invention are used as both the phosphorus ligand of the Group VIII transition metal complex catalyst and the free phosphorus ligand present in the reaction medium. In addition, it is to be understood that although the phosphorus ligand of the Group VIII transition metal-ionic phosphite ligand complex catalyst and free ionic phosphite ligand normally are the same, different ionic phosphite ligands, and mixtures thereof, may be used in the method of the invention.

The Group VIII transition metal-ionic phosphite ligand complex catalysts of this invention may be formed by methods known in the art. For instance, preformed Group VIII transition metal hydridocarbonyl ionic phosphite ligand complex catalysts may be prepared and introduced into the hydroformylation reaction medium. Preferably, the Group VIII transition metal-ionic phosphite ligand complex catalysts of this invention are derived from a metal catalyst precursor which may be introduced into the reaction medium for subsequent in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction medium along with the ionic phosphite ligand for the in situ formation of the active catalyst species.

In a more preferred embodiment, rhodium dicarbonyl acetylacetonate is reacted in the presence of an organic solvent with the ionic phosphite to form a catalytic rhodium carbonyl ionic phosphite acetylacetonate precursor. The precursor is introduced into the reactor along with excess free ionic phosphite ligand to form active catalyst in situ. Carbon monoxide, hydrogen, and ionic phosphite are ligands capable of forming complexes with the Group VIII transition metal, e.g., rhodium, and an active Group VIII transition metal-ionic phosphite ligand complex catalyst is present in the reaction medium under conditions of the hydroformylation process.

Moreover, it is clear that the amount of complex catalyst present in the reaction medium of a process of this invention need be only that minimum amount necessary to provide the given Group VIII transition metal in a concentration sufficient to catalyze the hydroformylation process. In general, Group VIII transition metal concentrations in the range of from about 10 ppm to about 10,000 ppm, calculated as free metal, should be sufficient for most hydroformylation processes. Moreover, in the rhodium catalyzed hydroformylation processes of this invention, it is generally preferred to employ from about 10 to 500 ppm of rhodium and more preferably from 25 to 350 ppm of rhodium, calculated as free metal.

Suitable olefinic starting materials or reactants for the hydroformylation processes of this invention can be terminally or internally unsaturated and have straight-chain, branched-chain, or cyclic structure as well as be olefin mixtures, such as obtained from the oligomerization of propene, butene, isobutene, etc., such as so called dimeric, trimeric or tetrameric propylene, codibutylene, and the like, as disclosed e.g. in U.S. Pat. Nos. 4,518,809 and 4,528,403. Such olefins can contain from 2 to 30 carbon atoms and may contain one or more ethylenically unsaturated groups. Moreover, such olefins may contain groups or substituents which do not unduly adversely interfere with the hydroformylation process, such as carbonyl, carbonyloxy, oxy, hydroxy, oxycarbonyl, halogen, alkoxy, aryl, haloalkyl, and the like. Illustrative olefinic unsaturated compounds are alpha-olefins, internal olefins, alkyl alkenoates, alkenyl alkenoates, alkenyl alkyl ethers, alkenols, and the like, e.g., ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-octene, styrene, dimeric propylene, trimeric propylene, tetrameric propylene, codibutylene, 3-phenyl-1-propene, 1,4-hexadiene, 1,7-octadiene, 3-cyclohexyl-1-butene, allyl alcohol, hex-1-en-4-ol, oc-1-en-4-ol, vinyl propionate, allyl propionate, allyl butyrate, methyl methacrylate, vinyl ethyl ether, vinyl methyl ether, allyl ethyl ether, n-propyl-7-octenoate, 3-butenenitrile, 5-hexenamide, and the like. Of course, mixtures of different olefinic staring materials can be used in the hydroformylation process of the subject invention. The subject invention is especially expected to be useful for the production of aldehydes by hydroformylating alpha-olefins and internal olefins containing from 6 to 30 carbon atoms.

The hydroformylation process of this invention is conducted in the presence of a solubilizing agent for the ionic phosphite ligand and the Group VIII transition metal-ionic phosphite ligand complex catalyst. Suitable solubilizing agents are described above.

Additional organic solvents may also be utilized, provided that they do not unduly adversely interfere with catalysis. Such organic solvents include those used in known Group VIII transition metal catalyzed processes. U.S. Pat. Nos. 3,527,809 and 4,148,830 disclose catalyzed hydroformylation processes. Mixtures of different organic solvents also may be utilized.

For instance aldehyde compounds corresponding to the desired aldehyde products and higher boiling aldehyde liquid condensation by-products produced in situ during the hydroformylation process typically are used as organic solvents in rhodium-catalyzed hydroformylation. Aldehydes and aldehyde trimers are preferred for start up of a continuous process. However, as hydroformylation proceeds, the solvent typically will comprise both aldehyde products and higher boiling aldehyde liquid condensation by-products due to the nature of such continuous processes. Such aldehyde condensation by-products can also be preformed; methods for their preparation are more fully described in U.S. Pat. Nos. 4,148,830 and 4,247,486.

It is further generally preferred to carry out the hydroformylation process of this invention in a continuous manner. Continuous processes are well-known in the art. Typically, olefinic starting material is hydroformylated with carbon monoxide and hydrogen in a non-aqueous liquid homogeneous reaction medium comprising the olefin, aldehyde product, higher boiling aldehyde condensation by-products, the Group VIII transition metal-ionic phosphite ligand complex catalyst, and free ionic phosphite ligand. Make-up quantities of the olefinic starting material, carbon monoxide, and hydrogen are supplied to the reaction medium. Reaction temperature and pressure conditions favorable to the hydroformylation of the olefinic starting material are established, and the desired aldehyde hydroformylation product is recovered in any manner desired.

The process can be carried out continuously in a single pass, i.e., a vaporous mixture comprising unreacted olefinic starting material and vaporized aldehyde product is removed from the liquid reaction medium and the aldehyde product is recovered, with make-up olefinic starting material, carbon monoxide, and hydrogen supplied to the liquid reaction medium for the next single reaction pass without recycling the unreacted olefinic starting material. However, a continuous process is preferred. Those skilled in the art recognize that continuous processes involving solely gas recycle are not readily suitable for hydroformylating higher olefins of, e.g., 6 to 30 carbon atoms, due to the low volatility of the aldehyde products.

Recycle procedures are well-known in the art and may involve the liquid phase recycling of the Group VIII transition metal-ionic phosphite ligand complex catalyst solution separated from the desired aldehyde reaction product or a gas recycle procedure, or a combination of both liquid and gas recycles as disclosed e.g. in U.S. Pat. Nos. 4,148,830, 4,247,486, and 4,593,127. The most preferred hydroformylation process of this invention comprises a continuous liquid rhodium catalyst recycle process.

The desired aldehyde product may be recovered in any conventional manner, such as those described e.g. in U.S. Pat. Nos. 4,148,830, 4,247,486, and 4,593,127. For instance, to continuously recycle liquid catalyst, the portion of the liquid reaction solution (containing aldehyde product, catalyst, etc.) removed from the reactor can be passed to a vaporizer/separator wherein the desired aldehyde product can be separated via distillation, in one or more stages, under normal, reduced, or elevated pressure, from the liquid reaction solution, condensed and collected in a product receiver, and further purified if desired. The remaining non-volatilized catalyst-containing liquid reaction solution then may be recycled back to the reactor together with any other volatile materials, e.g., unreacted olefin. Hydrogen and carbon monoxide separated from the liquid reaction solution as by distillation in any conventional manner can also be recycled. In general, desired aldehyde product may be separated from the rhodium catalyst containing product solution by selective vaporization of the aldehyde under reduced pressure and at temperatures below about 150° C., preferably below about 130° C.

Further, methods of separating catalyst and products which are not based on selective vaporization may be utilized. In the above-described hydroformylation processes, solubilized ionic phosphite ligands and catalysts comprising these ligands form homogeneous reaction solutions at reaction conditions. However, upon cooling, separate product and catalyst ligand phases may form. Alternatively, formation of separate product and catalyst ligand phases may also be induced by addition of a polar or non-polar phase compound such as an alcohol or hydrocarbon. When the non-aqueous hydroformylation reaction medium forms at least two organic liquid layers and causes separation of the catalyst components (rhodium, ligand, and organic solubilizing agent) in a first layer and the aldehyde product, possibly some aldehyde condensation by-product, and unreacted olefin in a second layer, catalyst components may be recovered by simple separation of the two organic layers, e.g. by decantation of one layer, without the need to employ distillation separation. The degree, or efficiency, of separation of a catalyst and ligand phase from a product phase may depend, inter alia, upon the temperature utilized to achieve the separation. Lower temperatures may yield better separation, but require greater cost to cool the stream being separated and to re-heat recycled catalyst and ligand. Obviously, the separation should not cause solidification of any component. With this guidance, those skilled in the art can select an appropriate separation temperature. Typically, separation may be carried out at about 40° C.

Hydroformylation processes of this invention are carried out in the presence of free ionic phosphite ligand, i.e., ligand that is not complexed with the Group VIII transition metal of the metal complex catalyst. This ligand may be any of the above-described ionic phosphite ligands. Thus, the hydroformylation process of this invention may be carried out in the presence of any quantity of free ligand. Typically, at least about one mol of free ligand per mol (gram-atom) of Group VIII transition metal is present in the reaction medium. Preferably, about 4 to about 100, and more preferably from about 10 to about 50 mols of free ligand per mol of Group VIII transition metal (e.g., rhodium) in the reaction medium is suitable for most purposes, particularly with regard to rhodium catalyzed hydroformylation. Of course, make-up ionic phosphite ligand can be supplied to the reaction medium of the hydroformylation process at any time and in any suitable manner, to maintain a predetermined level of free ligand in the reaction medium.

The reaction conditions for effecting the hydroformylation process of this invention may be those heretofore conventionally used and may comprise a reaction temperature of from about 45° to 200° C., preferably from about 50° C. to 150° C., and pressures ranging from about 1 to 10,000 psia, preferably from about 50 to 5,000 psia. The preferred reaction temperature will of course be dependent upon the identity of the olefinic starting material and metal catalyst and the efficiency desired. In general, it is preferred to employ a reaction temperature of from about 70° C. to about 120° C. in rhodium-catalyzed hydroformylation processes.

While optimization of reaction conditions to achieve the best results and the efficiency desired is dependent upon one's experience in the utilization of the subject hydroformylation invention, only routine experimentation should be necessary to ascertain conditions optimum for a given situation. Such experimentation is well within the knowledge of one skilled in the art and easily obtainable by following the more preferred aspects of this invention as explained herein.

For instance, the total gas pressure of hydrogen, carbon monoxide, and olefinic unsaturated starting materials for the hydroformylation process of this invention may range from about 1 to 10,000 psia, preferably from about 50 to about 5,000 psia. However, in the hydroformylation of olefins to produce aldehydes, it is preferred that the process be operated at a total gas pressure of hydrogen, carbon monoxide, and olefinic unsaturated starting material of between about 50 to 1500 psia, and more preferably between about 50 and 1000 psia. More specifically, the carbon monoxide partial pressure in the hydroformylation process of this invention is from about 1 to about 4000 psia, preferably from about 1 to about 500 psia, more preferably from about 1 to 120 psia, and most preferably between about 3 and 90 psia, while the hydrogen partial pressure typically is between about 1 and 4000 psia, preferably from about 10 to 500 psia, more preferably from about 10 to 160 psia, and most preferably between about 20 and 100 psia. In general, the $H_2:CO$ molar is at least about 1:10, and preferably the ratio ranges from about 1:10 to 100:1, more preferably from about 1:1 to about 10:1.

Finally, the aldehyde products of the hydroformulation process of this invention have a wide range of utility that is well-known and documented in the prior art. Aldehydes are especially useful as starting materials for the production of alcohols and acids.

The benefits of using ionic phosphite ligands in this invention are described above. The high catalyst activity and wide processing latitude afforded one in selecting the proper combination of conditions that will be most useful in obtaining a particular desired result is especially important. For instance, the ionic phosphite ligands can be used as the phosphorus ligand in non-aqueous rhodium catalyzed hydroformylation processes designed to produce aldehydes from both low as well as high molecular weight olefins at highly acceptable catalytic activity rates, at low hydroformylation pressures and low rhodium concentrations without unduly sacrificing processing efficiency and/or catalyst stability. Moreover, the low volatility of the ionic phosphite ligands of this invention (the ligands are virtually non-volatile, i.e., they normally will decompose before they can be volatilized) render them especially suitable for minimizing ligand and catalyst loss that can be experienced when conventional highly volatile phosphorus ligands are employed during the separation (via distillation) from the reactant mixture of low volatile aldehydes formed from high molecular weight ($C_6$–$C_{30}$) olefins. Alternatively, phase separation and decantation, as described above, can be utilized to separate catalyst and ligands from the remaining materials.

Discovery of a suitable ligand, such as the ionic phosphite ligands of this invention, which provide a metal-phosphorus complex catalyst for the hydroformylation of both low molecular weight and high molecular weight olefins, clearly minimizes the need to switch ligands or catalyst when one desires to change a commercial operation from producing low molecular weight aldehydes from low molecular weight olefins (e.g., $C_2$ to $C_5$ olefins) to one that is to produce high molecular weight aldehydes from high molecular weight olefins (e.g., C₆ and heavier olefins). Further, the ability to solubilize the ionic phosphite ligands used in this invention allows the non-aqueous hydroformylation process of this invention to be readily retrofitted to existing non-aqueous hydroformylation equipment without requiring major modifications.

The following examples are illustrative of the present invention and are not to be regarded as limiting. It is to be understood that all of the parts, percentages, and proportions referred to herein and in the appended claims are by weight unless otherwise indicated.

EXAMPLE I

Ionic phosphite ligands of the invention were prepared in accordance with the method disclosed herein. Each of the ligands was prepared using N-methylpyrrolidinone (NMP) as the aprotic solvent.

The phosphorus-containing intermediate utilized in Examples 1A and 1B was the 3,3'-di-tert-butyl-5,5'-dimethoxy-1,1'-biphenyl-2,2'-diyl chloridite which has the chemical formula and prepared as follows:

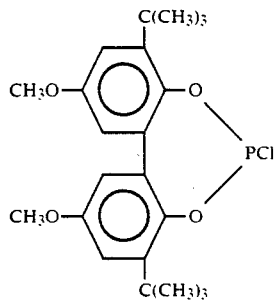

In one reaction vessel, about 120 grams of 2,2'-dihydroxy-3,3'-di-t-butyl-5,5'-dimethoxy-1,1'-biphenyl (0.335 mols) were reacted under a dry nitrogen atmosphere with 157 grams of triethylamine in toluene (about 800 mls). In a second vessel maintained under a dry nitrogen atmosphere, about 46 grams of PCl₃ (0.335 mols) were added to 250 mls of dry toluene. The mixture was placed in a Dry Ice and acetone bath and chilled to about −10° C. The first mixture was added to the second over a 45-minute period. The temperature was kept below about −10° C. during reaction.

The solid triethylamine hydrochloride salt which formed, (CH₃—CH₂)₃NHCl was readily separated from the solution by filtration. The remaining solution was concentrated on a Roto-Vap ® to yield about 125 grams of the above chloridite (90 percent pure). Thus-prepared chloridite was re-solubized in toluene and used in the following syntheses.

EXAMPLE 1A

4(sodium sulfonate) phenyl (3,3'-di-t-butyl-5,5'-dimethoxy-1,1'-biphenyl-2,2'-diyl) phosphite Ligand of the invention having the following formula

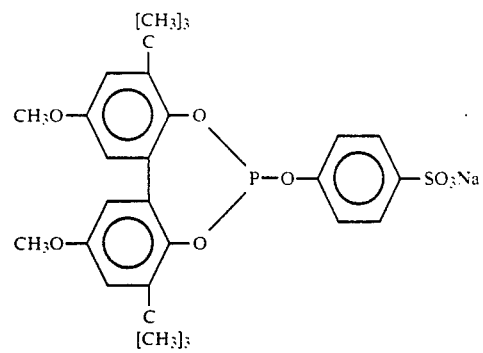

was made by establishing a dry reactor fitted with a stirrer and a condenser and placing 23.2 grams (0.1 mol) of 4-hydroxybenzenesulphonic acid, sodium salt dihydrate in 200 ml of NMP. A solution containing 20.0 grams of NaOH and 30.0 grams of water was separately prepared, and 10.0 grams (0.1 mols) of this solution was added to the NMP solution to form the p-phenolate sulfonate sodium double salt.

Solid precipitate formed after about 30 minutes of reaction time. Then 100 mls of toluene were added, and more precipitate formed. The mixture was heated to about 150° C. to azeotropically evaporate and remove toluene and water. The thus-treated double salt had a water concentration of 0.04 wt % and was a suspension of double salt in NMP.

The temperature of the suspension was adjusted to 42° C. and 94.75 grams of a portion of the above prepared toluene-chloridite solution containing about 0.1 mol of chloridite was added under a nitrogen atmosphere over a 20 minute period. Thereafter, the temperature was raised to about 85° C. over about a 2-hour period. Heating was discontinued and the mixture was allowed to cool.

Sodium chloride precipitate was separated from the solution by filtration. Then, NMP was evaporated using a Kugelrohr apparatus to produce 62 grams of a solid residue product. Recrystallization of the crude product from ethanol yielded 36.7 grams of pure product crystals, which were thoroughly dried using a Roto-Vap ®.

EXAMPLE 1B 2-t-Butyl-4(-potassium carboxylate) phenyl (3,3'-di-t-butyl-5,5'-dimethoxy-1,1'-biphenyl-2,2'-diyl) phosphite Ionic diorganophosphite having the formula

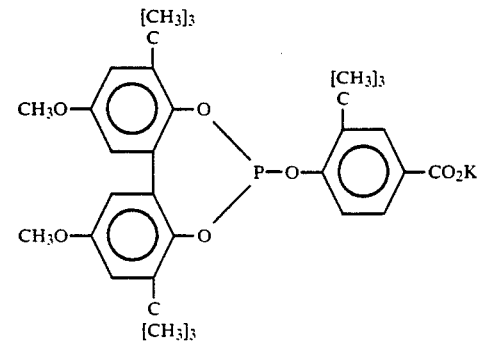

was prepared in essentially the same manner as Example 1A. A quantity (10.0 grams, 0.049 mols) of 3-t-butyl-4-hydroxybenzoic acid was dissolved in 150 mls of NMP. About 5.45 grams (0.097 mols) of a 40 wt percent aqueous solution of KOH was added to the solution to form the dipotassium salt of 3-tert-butyl-4-hydroxybenzoic acid. Toluene was added to this mixture, which was then heated to 165° C. to azeotropically distill water and toluene. The thus-dried suspension of double salt in NMP was transferred to a dry vessel and the temperature was adjusted to about 62° C.

A portion of the above prepared toluene-chloridite solution (45.99 grams, 0.049 mols) was added dropwise over an 8 minute period. The reaction mixture was heated to maintain a temperature above 50° C. for about 20 minutes. Then, the mixture was allowed to cool. Then, NMP was evaporated using a Kugelrohr apparatus to an oily liquid, which turns into solid upon standing at ambient conditions. About 34.8 grams of crude product were recovered.

The crude product was dissolved in about 400 mls of methanol, and some insoluble material was removed by filtration. The methanol solution was chilled to about 5° C. and purified crystals were recovered.

EXAMPLE 1C

Open-ended bis-phosphite having the formula

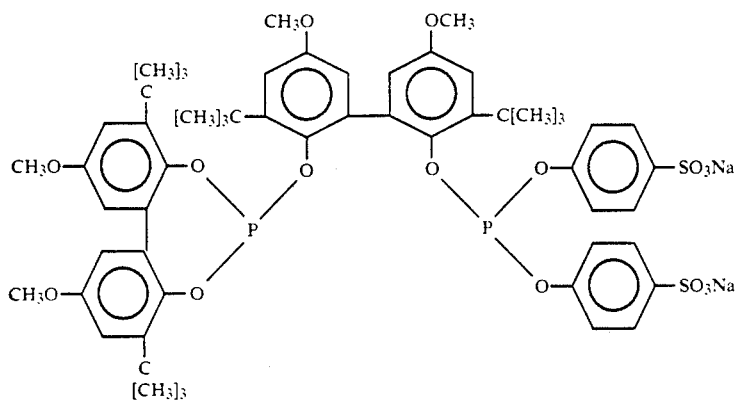

was prepared in essentially the same manner as in Example 1A. A toluene solution of a dichloridite having the formula

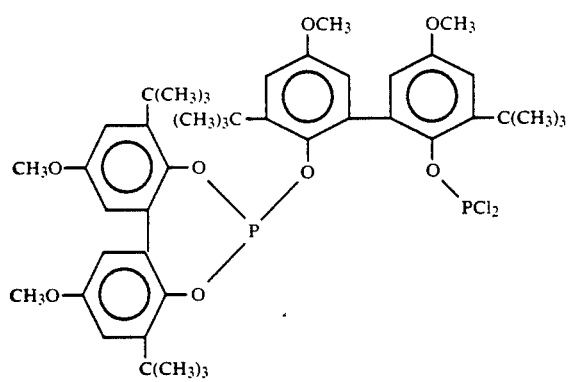

was separately prepared in a similar manner as the toluene-chloridite solution of Example 1.

4-Hydroxybenzene sulfonic acid, sodium salt (16.96 grams, 0.073 mols) was dissolved in 200 mls of NMP. About 2.92 grams (0.073 mols) of a forty percent aqueous NaOH solution was added, the mixture was stirred for about 45 minutes, and the double salt produced. One hundred mls of toluene were added to the mixture, which then was heated to 165° C. to azeotropically distill water and toluene.

The dichloridite solution (0.037 mols) was added to the double salt suspension dropwise after the temperature had been adjusted to about 40° C. After 15 minutes, all the dichloridite solution had been added, and the reaction mixture was heated to about 90° C. in about 90 minutes.

Upon cooling to ambient temperature and stripping the NMP in a Kugelrohr apparatus, about 39.2 grams of crude product was recovered.

EXAMPLE II

A series of various rhodium complex catalyst precursor solutions consisting essentially of the solubilized reaction product of rhodium dicarbonyl acetylacetonate and three ionic phosphite ligands (this invention) were prepared and used to hydroformylate olefins aldehydes in the following manner.

Rhodium dicarbonyl acetylacetonate was mixed at ambient temperature with the ionic phosphite ligands having the formulae described in Examples I-A, I-B, and I-C. Sufficient Texanol® (Eastman brand 2,2,4-trimethyl-1,3-pentanediol monoisobutyrate) and TPEG-990® (Union Carbide Corporation polyethylene glycol) was added as solvent to produce the various rhodium catalytic precursor solutions containing the amounts of rhodium and ligands shown in Table I below.

Each rhodium catalytic precursor solution so prepared was then used to hydroformylate olefins in a magnetically stirred, 100 mL capacity, stainless steel autoclave which was attached to a gas manifold for introducing gases to the desired partial pressures. The autoclave was also equipped with a pressure calibrator for determining reaction pressure and a platinum resistance thermometer for determining reactor solution temperature. The reactor was heated externally by two 300 watt heating bands. The reactor solution temperature was controlled by a platinum resistance sensor connected to an external proportional temperature controller for controlling the temperature of the external band heaters.

In each non-aqueous hydroformylation reaction, about 15 milliliters (about 14 grams) of the rhodium catalytic precursor solution was charged to the autoclave reactor under nitrogen and heated to the reaction temperature employed (as given in Table I below). The reactor was then vented down to 5 psia and 5 ml olefin were added with a syringe. A premixed gas mixture of 1:1 carbon monoxide:hydrogen was introduced into the reactor via the gas manifold and the olefin so hydroformylated.

The hydroformylation reaction rate expressed in the table in gram-mols per liter per hour of aldehydes produced was determined from sequential 5 psia pressure drops in the reactor spanning the nominal reactor operating pressure, while the mol ratio of linear to branched product (N/I ratio) was measured by gas chromatography and the results are given in Table 1 below.

TABLE I

Hydroformylation of Different Olefins Using Ionic Phosphites

| Catalyst No. | Olefin | Temp. °C. | Pressure, psia | | Rate | N/I Ratio |
|---|---|---|---|---|---|---|
| | | | H₂ | CO | | |
| 3 | Tetradecene-1 | 80 | 40 | 40 | 0.66 | 1.3 |
| 2 | Octene-2 | 100 | 50 | 50 | 0.32 | 11.9 |
| 1 | Octene-2 | 100 | 50 | 50 | 1.69 | 0.8 |
| 2 | Isobutene | 100 | 40 | 40 | 1.02 | one product |
| 1 | Isobutene | 100 | 40 | 40 | 0.90 | one product |
| 3 | Octene-1 | 90 | 40 | 40 | 4.03 | 1.5 |
| 3 | Hexene-1 | 70 | 50 | 50 | 0.63 | 1.9 |
| 2 | Vinyl acetate | 100 | 40 | 40 | 1.45 | one product |

Catalyst No. 1 contains 2 wt % ligand of Example I-A, 400 ppm Rh, and 30 wt % TPEG-990 ® in Texanol ®

Catalyst No. 2 contains 4 wt % ligand of Example I-C, 400 ppm Rh, and 30 wt % TPEG-990 ® in Texanol ®

Catalyst No. 3 contains 4 wt % ligand of Example I-B, 200 ppm Rh, 50 wt % TPEG-990 ®, and 10 wt % "18-Crown-6" in Texanol ®

EXAMPLE III

Continuous hydroformylation of olefins using ionic phosphite ligands was conducted in the following manner.

The non-aqueous hydroformylation was conducted in a glass reactor operating in a continuous single pass hydroformylation mode. The reactor consisted of a three-ounce pressure bottle submersed in an oil bath with a glass front for viewing. About 20-mL of a freshly prepared rhodium catalytic precursor solution was charged to the reactor with a syringe, after purging the system with nitrogen. The precursor solution contained the concentration of rhodium described in Table 2 below, introduced as rhodium dicarbonyl acetylacetonate, about 2 to 4 weight percent of the ionic phosphite ligands described in Examples I-A, I-B, and I-C, and Texanol®-TPEG-990® as the solvent. After closing the reactor, the system was again purged with nitrogen and the oil bath was heated to furnish the desired hydroformylation reaction temperature. The hydroformylation reaction was conducted with the partial pressures (psia) of hydrogen, carbon monoxide, and olefin being given in Table II below.

The flows of the feed gases (carbon monoxide, hydrogen, olefin, and nitrogen) were controlled individually with mass flow meters and the feed gases dispersed into the reaction solution via microporous stainless steel spargers. The reaction temperatures are given in Table II below. The approximate average reaction rates, in gram-mols per liter per hour of product aldehyde, as well as the linear to branched aldehyde product ratio, are given in Table II below.

TABLE II

Continuous Olefin Hydroformylation Using Ionic Phosphite Ligands of Examples I-A, I-B, and I-C.

| Ligand | Olefin | Pressure, psia | | | Rh conc. ppm | Temp. °C | Rate | N/I Ratio |
|---|---|---|---|---|---|---|---|---|
| | | Olefin | CO | H₂ | | | | |
| I-A | Propylene | 7 | 40 | 41 | 300 | 83 | 7 | 1.4 |
| I-B | Propylene | 14 | 42 | 44 | 150 | 83 | 3.8 | 0.9 |
| I-C | Propylene | 10 | 38 | 38 | 150 | 83 | 3.0 | 20 |
| I-A | Butene-2 | 14 | 38 | 45 | 300 | 100 | 1.0 | 0.7 |
| I-B | Butene-2 | 25 | 30 | 40 | 300 | 100 | 1.2 | 0.6 |
| I-C | Butene-2 | 9 | 47 | 52 | 300 | 100 | 0.3 | 8 |

Although preferred embodiments of this invention have been discussed herein, those skilled in the art will appreciate that changes and modifications may be made without departing from the spirit and scope of this invention.

What is claimed is:

1. In a non-aqueous homogeneous transition metal catalyzed process which comprises employing a non-aqueous reaction medium containing an organic solubilized Group VIII transition metal-phosphorus ligand complex catalyst, the improvement comprising employing as the phosphorus ligand a low-volatile, organic solubilized ionic phosphite ligand selected from the group consisting of (i) poly-phosphites having the formula

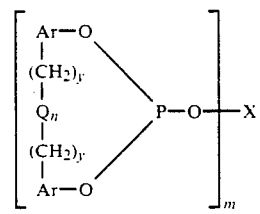

(I)

wherein each Ar group represents an identical or different aryl radical; wherein X represents a m-valent hydrocarbon radical selected from the group consisting of alkylene, alkylene-oxy-alkylene, aryl, and aryl-$(CH_2)_y$—$(Q)_n$—$(CH_2)_y$-aryl; wherein each y individually has a value of 0 or 1; wherein each Q individually represents a divalent bridging group selected from the class consisting of —$CR^1R^2$—, —O—, —S—, $NR^3$, —$SiR^4R^5$, and —CO—, wherein $R^1$ and $R^2$ each individually represents a radical selected from the group consisting of hydrogen, alkyl of 1 to 12 carbon atoms, phenyl, tolyl and anisyl, wherein $R^3$, $R^4$, and $R^5$ each individually represents —H or —$CH_3$; wherein each n individually has a value of 0 to 1; wherein m has a value of 2 to 6; and wherein the poly-phosphites of formula (I) contain at least one ionic moiety selected from the group consisting of salts of carboxylic acid and of sulfonic acid substituted on an aryl moiety of Ar or X;

(ii) diorganophosphites having the formula

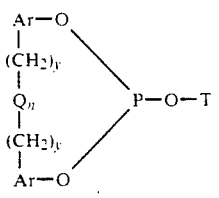
(II)

wherein T represents a monovalent hydrocarbon radical; wherein Ar, Q, n and y are as defined above; and wherein the diorganophosphites of formula (II) contain at least one ionic moiety selected from the group consisting of salts of carboxylic acid and of sulfonic acid substituted on any aryl moiety of Ar or T; and (iii) open-ended bis-phosphites having the formula

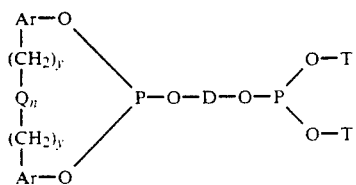
(III)

wherein D represents a divalent bridging group selected from the group consisting of alkylene, aryl, and aryl-$(CH_2)_y$—$Q_n$—$(CH_2)_y$-aryl; wherein Ar, Q, n, y, and T are as defined above and each T may be identical or different; and wherein the bis-phosphites of formula (III) contain at least one ionic moiety selected from the group consisting of salts of carboxylic acid and of sulfonic acid substituted on an aryl moiety of Ar, D or T; and wherein said salts contain that number of cations needed to balance the charge of the acid anions substituted onto the phosphite ligand, said cations being selected from the group consisting of alkali metals, alkaline earth metals, and quaternary ammonium cations.

2. In a non-aqueous hydroformylation process for producing aldehydes which comprises reacting an olefinically unsaturated organic compound with carbon monoxide and hydrogen, in a non-aqueous hydroformylation reaction medium containing an organic solubilized Group VIII transition metal-phosphorus ligand complex catalyst and free phosphorus ligand, the improvement comprising employing as the phosphorus ligand of said complex catalyst and as said free phosphorus ligand, a low-volatile, organic solubilized ionic phosphite ligand selected from the group consisting of (i) poly-phosphites having the formula

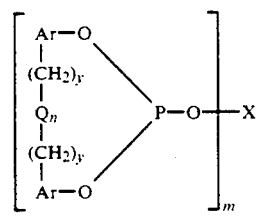
(I)

wherein each Ar group represents an identical or different aryl radical; wherein X represents a m-valent hydrocarbon radical selected from the group consisting of alkylene, alkylene-oxy-alkylene, aryl, and aryl-$(CH_2)_y$—$(Q)_n$—$(CH_2)_y$-aryl; wherein each y individually has a value of 0 or 1; wherein each Q individually represents a divalent bridging group selected from the class consisting of —$CR^1R^2$—, —O—, —S—, $NR^3$, —$SiR^4R^5$, and —CO—, wherein $R^1$ and $R^2$ each individually represents a radical selected from the group consisting of hydrogen, alkyl of 1 to 12 carbon atoms, phenyl, tolyl and anisyl, wherein $R^3$, $R^4$, and $R^5$ each individually represents —H or —$CH_3$; wherein each n individually has a value of 0 to 1; wherein m has a value of 2 to 6; and wherein the poly-phosphites of formula (I) contain at least one ionic moiety selected from the group consisting of salts of carboxylic acid and of sulfonic acid substituted on an aryl moiety of Ar or X;

(ii) diorganophosphites having the formula

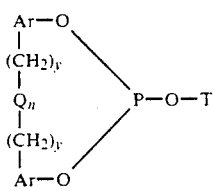
(II)

wherein T represents a monovalent hydrocarbon radical; wherein Ar, Q, n and y are as defined above; and wherein the diorganophosphites of formula (II) contain at least one ionic moiety selected from the group consisting of salts of carboxylic acid and of sulfonic acid, substituted on any aryl moiety of Ar or T; and (iii) open-ended bis-phosphites having the formula

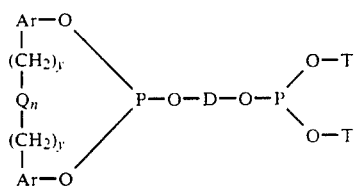
(III)

wherein D represents a divalent bridging group selected from the group consisting of alkylene, aryl, and aryl-$(CH_2)_y$—$Q_n$—$(CH_2)_y$-aryl; wherein Ar, Q, n, y, and T are as defined above and each T may be identical or different; and wherein the bis-phosphites of formula (III) contain at least one ionic moiety selected from the group consisting of salts of carboxylic acid and of sulfonic acid substituted on an aryl moiety of Ar, D or T; and wherein said salts contain that number of cations needed to balance the charge of the acid anions substituted onto the phosphite ligand, said cations being selected from the group consisting of alkali metals, alkaline earth metals, and quaternary ammonium cations.

3. A process as defined in claim 2, wherein the Group VIII transition metal is rhodium, wherein the olefinically unsaturated compound contains from 2 to 30 carbon atoms, and wherein the reaction temperature is from about 70° C. to about 120° C.; wherein the total gas pressure of hydrogen, carbon monoxide, and olefinically unsaturated compound is less than about 500 psia; wherein the carbon monoxide partial pressure is from about 1 to 120 psia; and the hydrogen partial pressure is from about 1 to 160 psia.

4. A process as defined in claim 3 wherein the olefinically unsaturated compound is an alpha-olefin containing from 2 to 5 carbon atoms.

5. A process as defined in claim 3, wherein the olefinically unsaturated compound is an alpha-olefin containing from 6 to 30 carbon atoms.

6. A process as defined in claim 5 wherein the low-volatile, organic solubilized ionic phosphite ligand is a ligand selected from the group consisting of

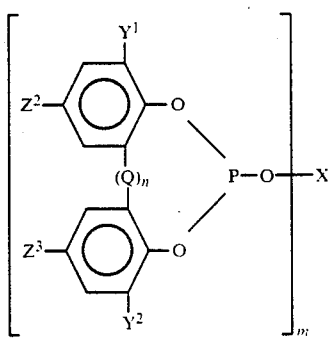
(I-A)

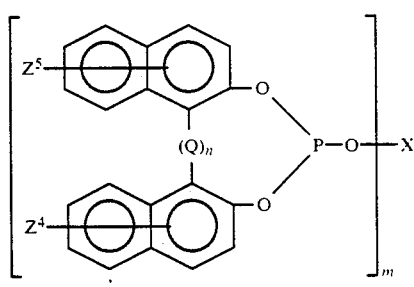
(I-B)

wherein each $Y^1$, $Y^2$, $Z^2$, $Z^3$, $Z^4$ and $Z^5$ group individually represents a radical selected from the group consisting of hydrogen, monovalent hydrocarbon radicals containing from 1 to 18 carbon atoms, hydroxy, alkoxy radicals containing from 1 to 10 carbon atoms, and salts of sulfonic acid and of carboxylic acid; wherein m is 2 and X is selected from the group consisting of divalent aryl and aryl-$Q_n$-aryl radicals containing from 6 to 30 carbon atoms; wherein each Q radical individually represents —$CR^1R^2$— wherein $R^1$ and $R^2$ each individually represent a radical selected from the group consisting of hydrogen and alkyl of 1 to 12 carbon atoms; and wherein n is 0 or 1; with the proviso that in each phosphite ligand of formulae I-A and I-B above, either at least one $Y^1$, $Y^2$, $Z^2$, $Z^3$, $Z^4$ and $Z^5$ group is an ionic moiety selected from the group consisting of the alkali metal and alkaline earth metal salts of sulfonic acid and of carboxylic acid, or each said ligand contains at least one such ionic moiety substituted on an aryl moiety of X; and wherein each said ligand contains from 1 to 3 such ionic moieties.

7. A process as defined in claim 5 wherein the low-volatile, organic solubilized ionic phosphite ligand is a ligand selected from the group consisting of

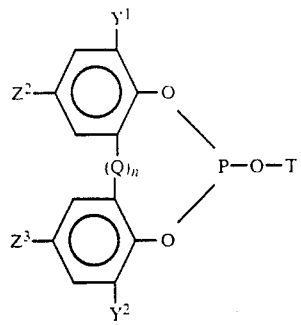
(II-A)

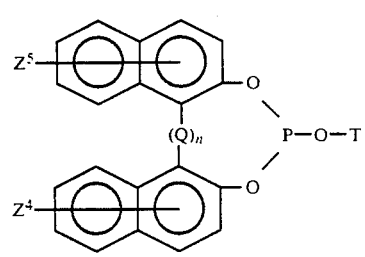
(II-B)

wherein each $Y^1$, $Y^2$, $Z^2$, $Z^3$, $Z^4$ and $Z^5$ group individually represents a radical selected from the group consisting of hydrogen, monovalent hydrocarbon radicals containing from 1 to 18 carbon atoms, hydroxy, alkoxy radicals containing from 1 to 10 carbon atoms, and salts of sulfonic acid and of carboxylic acid; wherein each Q radical individually represents —$CR^1R^2$— wherein $R^1$ and $R^2$ each individually represent a radical selected from the group consisting of hydrogen and alkyl of 1 to 12 carbon atoms; and wherein n is 0 or 1; wherein each T radical individually represents a monovalent hydrocarbon radical containing from 1 to 30 carbon atoms selected from the group consisting of alkyl, aryl, aralkyl, alkaryl and cycloalkyl radicals; with the proviso that in each phosphite ligand of formulae II-A and II-B above, either at least one $Y^1$, $Y^2$, $Z^2$, $Z^3$, $Z^4$ and $Z^5$ group is an ionic moiety selected from the group consisting of alkali metal and alkaline earth metal salts of sulfonic acid and of carboxylic acid, or each said ligand contains at least one such ionic moiety substituted on an aryl moiety of T; and wherein each said ligand contains from 1 to 3 such ionic moieties.

8. A process as defined in claim 5 wherein the low-volatile, organic solubilized ionic phosphite ligand is a ligand selected from the group consisting of

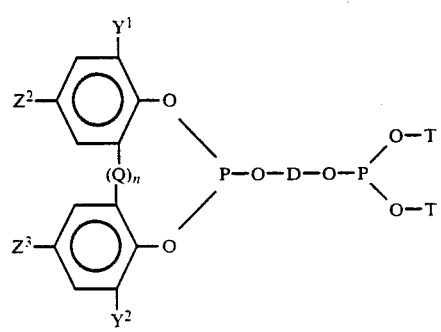
(III-A)

-continued

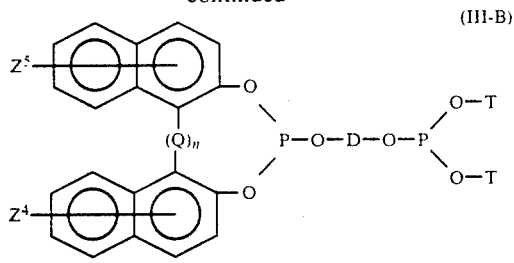

(III-B)

wherein each $Y^1$, $Y^2$, $Z^2$, $Z^3$, $Z^4$ and $Z^5$ group individually represents a radical selected from the group consisting of hydrogen, monovalent hydrocarbon radicals containing from 1 to 18 carbon atoms, hydroxy, alkoxy radicals containing from 1 to 10 carbon atoms, and salts of sulfonic acid and of carboxylic acid; wherein Q represents —$CR^1R^2$— wherein $R^1$ and $R^2$ each individually represent a radical selected from the group consisting of hydrogen and alkyl of 1 to 12 carbon atoms; wherein the divalent bridging group D contains from 6 to 30 carbon atoms and is selected from the group consisting of aryl and aryl-$Q_n$-aryl radicals; wherein each T radical individually represents a monovalent hydrocarbon radical containing from 1 to 30 carbon atoms selected from the group consisting of alkyl, aryl, aralkyl, alkaryl, and cycloalkyl radicals, and wherein each T maybe the same or different; and wherein n is 0 or 1; with the proviso that in each phosphite ligand of formulae III-A and III-B above, either at least one $Y^1$, $Y^2$, $Z^2$, $Z^3$, $Z^4$ and $Z^5$ group is an ionic moiety selected from the group consisting of the alkali metal and alkaline earth metal salts of sulfonic acid and a carboxylic acid, or each said ligand contains at least one such ionic moiety substituted on an aryl moiety of D or T; and wherein each said ligand contains from 1 to 3 such ionic moieties.

9. A process as defined in claim 6 wherein the ligand contains only one such ionic moiety which is a salt of sulfonic acid.

10. A process as defined in claim 7 wherein the ligand contains only one such ionic moiety which is a salt of sulfonic acid.

11. A process as defined in claim 8 wherein the ligand contains only one such ionic moiety which is a salt of sulfonic acid.

12. A process as defined in claim 2 wherein the ionic phosphite ligand has the formula

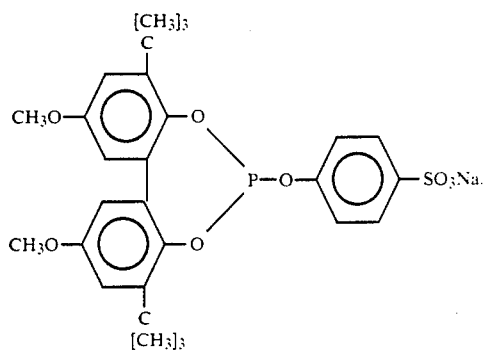

13. A process as defined in claim 2 wherein the ionic phosphite ligand has the formula

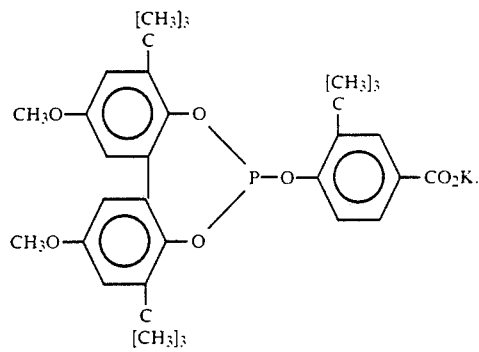

14. A process as defined in claim 2 wherein the ionic phosphite ligand has the formula

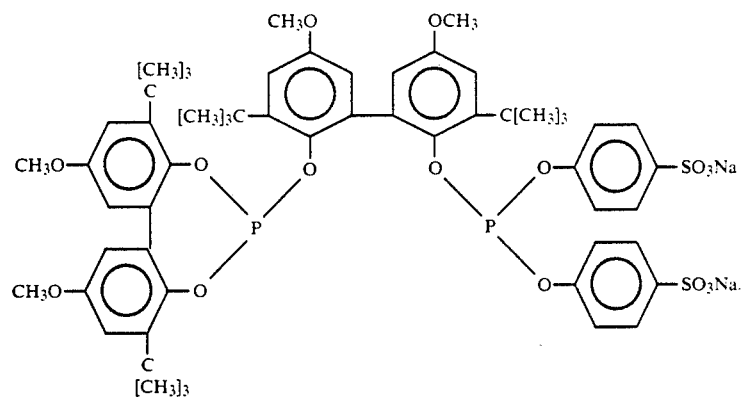

* * * * *